(12) United States Patent
Nakahata et al.

(10) Patent No.: US 8,741,644 B2
(45) Date of Patent: Jun. 3, 2014

(54) METHOD FOR PRODUCING MAST CELLS FROM PLURIPOTENT STEM CELLS

(75) Inventors: Tatsutoshi Nakahata, Kyoto (JP); Kohichiro Tsuji, Tokyo (JP); Feng Ma, Tokyo (JP)

(73) Assignee: Kyoto University, Kyoto (JP)

( * ) Notice: Subject to any disclaimer, the term of this patent is extended or adjusted under 35 U.S.C. 154(b) by 0 days.

(21) Appl. No.: 13/394,666

(22) PCT Filed: Sep. 8, 2010

(86) PCT No.: PCT/JP2010/065893
§ 371 (c)(1),
(2), (4) Date: May 2, 2012

(87) PCT Pub. No.: WO2011/030915
PCT Pub. Date: Mar. 17, 2011

(65) Prior Publication Data
US 2012/0208206 A1 Aug. 16, 2012

Related U.S. Application Data

(60) Provisional application No. 61/240,376, filed on Sep. 8, 2009.

(51) Int. Cl.
*C12N 5/00* (2006.01)
*C12N 5/02* (2006.01)
*C12N 5/0787* (2010.01)

(52) U.S. Cl.
CPC .......... *C12N 5/0642* (2013.01); *C12N 2506/02* (2013.01); *C12N 2506/03* (2013.01); *C12N 2506/45* (2013.01); *C12N 2501/125* (2013.01); *C12N 2501/145* (2013.01); *C12N 2501/23* (2013.01); *C12N 2501/26* (2013.01)
USPC ........... 435/377; 435/373; 435/375; 435/325; 435/383; 435/384; 435/372

(58) Field of Classification Search
CPC .................................................. C12N 5/0642
See application file for complete search history.

(56) References Cited

U.S. PATENT DOCUMENTS

2007/0015280 A1   1/2007   Rossi
2009/0068742 A1   3/2009   Yamanaka
2009/0275131 A1   11/2009  Daigh et al.

FOREIGN PATENT DOCUMENTS

| WO | 2007-069666 | 6/2007 |
| WO | 2009/135206 | 11/2009 |
| WO | 2009/137624 | 11/2009 |
| WO | 2010/099539 | 9/2010 |

OTHER PUBLICATIONS

Sawai et al. 1999, Blood 93(11): 3703-3712.*
Orlovskaya (2008, Methods, 45:159-167.*
Xu 1998, Blood, 92:2032-2040.*
H. Saito et al., "Selective Growth of Human Mast Cells Induced by Steel Factor, IL-6, and Prostaglandin $E_2$ from Cord Blood Mononuclear Cells", The Journal of Immunology, vol. 157, pp. 343-350, 1996.
K. Takahashi et al., "Induction of Pluripotent Stem Cells from Adult Human Fibroblasts by Defined Factors", Cell, vol. 131, pp. 861-872, Nov. 30, 2007.
Supplementary European Search Report issued Jul. 19, 2013 in corresponding European Application No. 10 81 5504.
Yoshikubo et al., "Differentiation and maintenance of mast cells from $CD34^+$ human cord blood cells", Experimental Hematology, vol. 34, 2006, pp. 320-329.
Choi et al., "Hematopoietic and Endothelial Differentiation of Human Induced Pluripotent Stem Cells", Stem Cells, vol. 27, 2009, pp. 559-567.
Tsiftsoglou et al., "Multilevel targeting of hematopoietic stem cell self-renewal, differentiation and apoptosis for leukemia therapy", Pharmacology & Therapeutics, vol. 122, 2009, pp. 264-280.
International Search Report and Written Opinion dated Nov. 22, 2010 in International (PCT) Application No. PCT/JP2010/065893.
F. Ma et al., "Novel Method for Efficient Production of Multipotential Hematopoietic Progenitors From Human Embryonic Stem Cells", International Journal of Hematology, vol. 85, No. 5, pp. 371-379, 2007.
F. Ma et al., "Differentiation Induction of Mast Cells from Human es Cells", Inflammation and Regeneration, vol. 27, No. 4, pp. 398, 59, Jul. 2007 with English translation.
F. Ma et al., "Direct Development of Functionally Mature Tryptase/Chymase Double-Positive Connective Tissue-Type Mast Cells from Primate Embryonic Stem Cells", Stem Cells, vol. 26, No. 3, pp. 706-714, 2008.
K. Umeda et al., "Development of Primitive and Definitive Hematopoiesis from Non-Human Primate Embryonic Stem Cells In Vitro", Development and Disease, vol. 131, No. 8, pp. 1869-1879, 2004.
D. Kempuraj et al., "Characterization of Mast Cell-Committed Progenitors Present in Human Umbilical Cord Blood", Blood, vol. 93, No. 10, pp. 3338-3346, May 15, 1999.
B. Durand et al., "Long-Term Generation of Human Mast Cells is Serum-Free Cultures of $CD34^+$ Cord Blood Cells Stimulated with Stem Cell Factor and Interleukin-3", Blood, vol. 84, No. 11, pp. 3667-3674, Dec. 1, 1994.
J. Lappalainen et al., "A Protocol for Generating High Numbers of Mature and Functional Human Mast Cells from Peripheral Blood", Clinical and Experimental Allergy, vol. 37, No. 9, pp. 1404-1414, 2007.

(Continued)

*Primary Examiner* — Valarie Bertoglio
(74) *Attorney, Agent, or Firm* — Wenderoth, Lind & Ponack, L.L.P.

(57) ABSTRACT

The present invention relates to a method for producing human mast cells from human pluripotent stem cells. More particularly, the present invention provides a method for producing human mast cells from human pluripotent stem cells, comprising the steps of: (a) culturing human pluripotent stem cells under a condition suitable for promoting differentiation of the human pluripotent stem cells into hematopoietic progenitor cells expressing CD34; and (b) culturing the cells obtained in step (a) in the presence of hematopoietic factors comprising thrombopoietin (TPO) and Flt3 ligand.

5 Claims, 13 Drawing Sheets

(56) References Cited

OTHER PUBLICATIONS

N. Kanbe et al., "Establishment of Culturing Method of Connective Tissue Type Human Mast Cells", The Japanese Journal of Allergology, vol. 50, pp. 909, 41, 2001 with English translation.

A. Li et al., "Functional Analysis of Histamine Release from Basophils and Mast Cells in Subjects with the Ile-181→Leu Variant of FcεRI-β", Clinical Science, vol. 93, pp. 279-286, 1997.

K. Takahashi et al., "Induction of Pluripotent Stem Cells from Mouse Embryonic and Adult Fibroblast Cultures by Defined Factors", Cell, vol. 126, pp. 663-676, Aug. 25, 2006.

* cited by examiner

A: AGM-S3    B: 253G1

A: May-Geimsa  B: Tuluidine Blue  C: Alcian Blue

A

IgE-R (CRA-1)

B

Cathepsin-G

C

CD203c

D

Carboxypeptidase-A

E

CD88

METHOD FOR PRODUCING MAST CELLS FROM PLURIPOTENT STEM CELLS

This application is a U.S. national stage of International Application No. PCT/JP2010/065893 filed Sep. 8, 2010, which claims the benefit of U.S. provisional application Ser. No. 61/240,376 filed Sep. 8, 2009.

TECHNICAL FIELD

The present invention relates to a method for producing human mast cells from human pluripotent stem cells. More particularly, the present invention relates to a method for producing human mast cells from human pluripotent stem cells, comprising the steps of: (a) culturing human pluripotent stem cells under a condition suitable for promoting differentiation of the human pluripotent stem cells into hematopoietic progenitor cells expressing CD34; and (b) culturing the cells obtained in step (a) in the presence of hematopoietic factors comprising thrombopoietin (TPO) and Flt3 ligand.

BACKGROUND ART

It is said that not less than 20% of the population has abnormalities in allergic reactions, which are primary causes of asthma, pollinosis, rhinitis and dermatitis, and this has become a social problem. In these allergic reactions, an antigen such as house dust or pollen is bound to IgE, and the resulting complex acts on IgE receptors on mast cells, leading to activation of the mast cells. The activated mast cells release various chemical mediators such as histamine to cause development of allergic reactions and inflammatory conditions.

Thus, it is necessary to use mast cells for development and evaluation of therapeutic agents for allergic diseases. Therefore, to prepare mast cells, induction of differentiation from umbilical cord blood (1) and induction of differentiation from monkey ES cells (2) have been attempted.

In recent years, induced pluripotent stem cells (iPS cells) of mouse and human have been established by introduction of the Oct3/4, Sox2, Klf4 and c-Myc genes into fibroblasts and their forced expression therein (3, 4, 5).

However, there has been no report of successful induction of differentiation of human iPS cells into human mast cells so far.

REFERENCES

1. Saito H. et al., *J Immunol.*, 157: 343-350 (1996)
2. FENG M A, et al., *STEM CELLS*, 26: 706-714 (2008)
3. WO 2007/069666 A1
4. Takahashi, K. and Yamanaka, S., *Cell*, 126: 663-676 (2006)
5. Takahashi, K. et al., *Cell*, 131: 861-872 (2007)

SUMMARY OF THE INVENTION

The present invention aims to efficiently produce mast cells from pluripotent stem cells. Therefore, an object of the present invention is to provide culture methods by which differentiation of human pluripotent stem cells, especially human iPS cells, into mast cells is induced efficiently.

In order to solve the above object, the present inventors first co-cultured iPS cells with cells separated from the AGM region of a mouse fetus, and then culturing the obtained cells by suspension culture in a medium supplemented with appropriate cytokines. Subsequently, using a serum-free medium supplemented with appropriate cytokines comprising thrombopoietin (TPO), but not IL-3, culture was carried out for additional more than 4 weeks to induce differentiation to mast cells. As a result, cells expressing cell surface markers unique to mast cells were established at an efficiency of more than 80%.

Based on the above findings, the present inventors cultured iPS cells under appropriate culture conditions and induced their differentiation in a stepwise manner. Thereby, the present inventors succeeded in efficient production of mast cells, thereby completed the present invention.

An aspect of the present invention is to provide a method for producing human mast cells from human pluripotent stem cells, comprising the steps of:

(a) culturing human pluripotent stem cells under a condition suitable for promoting differentiation of the human pluripotent stem cells into hematopoietic progenitor cells expressing CD34; and (b) culturing the cells obtained in step (a) in the presence of hematopoietic factors comprising thrombopoietin (TPO) and Flt3 ligand.

Another aspect of the present invention is to provide the method as described above, wherein the condition in the step (a) is co-culture with cells obtained from the AGM region of a mammalian fetus in the presence of vascular endothelial growth factor (VEGF).

Another aspect of the present invention is to provide the method as described above, wherein said hematopoietic factors of step (b) further comprise stem cell factor (SCF) and IL-6.

Another aspect of the present invention is to provide the method as described above, wherein the step (b) comprises the following sequential steps of:

(1) suspension-culturing in the presence of the hematopoietic factors comprising TPO, Flt3 ligand, SCF, IL-6 and IL-3; and (2) suspension-culturing in a serum-free medium containing the hematopoietic factors comprising TPO, Flt3 ligand, SCF, and IL-6 but not IL-3.

Another aspect of the present invention is to provide the method as described above, wherein said cells obtained from the AGM region of a mammalian fetus is AGM-S3.

Another aspect of the present invention is to provide the method as described above, wherein said human pluripotent stem cells are human induced pluripotent stem cells.

Another aspect of the present invention is to provide the method as described above, wherein the produced human mast cells express c-kit, tryptase, chymase, IgE receptor, Cathepsin-G, CD203c, Carboxypeptidase-A and CD88.

Another aspect of the present invention is to provide a method for screening a test substance having at least one of the actions selected from the group consisting of (a) apoptosis induction, (b) degranulation inhibition and (c) inhibition of production of inflammatory mediators, comprising contacting the human mast cells produced from human induced pluripotent stem cells by the method according to claim 1 with test substances, measuring at least one of said actions of the test substance, and selecting a test substance at least one of said actions.

Another aspect of the present invention is to provide the method as described above, wherein said human induced pluripotent stem cells are produced from somatic cells of a subject suffering from bronchial asthma, allergic disease or atopic dermatitis.

Another aspect of the present invention is to provide the method as described above, wherein said test substances are therapeutic agents for bronchial asthma, allergic disease or atopic dermatitis.

Another aspect of the present invention is to provide the method as described above, wherein said human induced pluripotent stem cells have a mutation in the FcεRI β chain.

DESCRIPTION OF THE PREFERRED EMBODIMENTS

Figure 1:
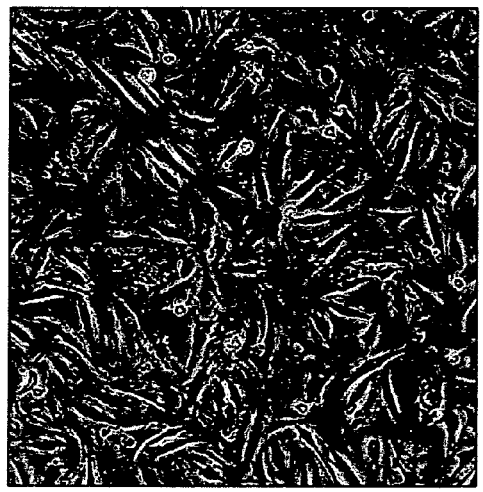
FIG. 1 shows phase contrast micrographs of AGM-3 (A) and human iPS cells 253G1 (B).
Figure 1:
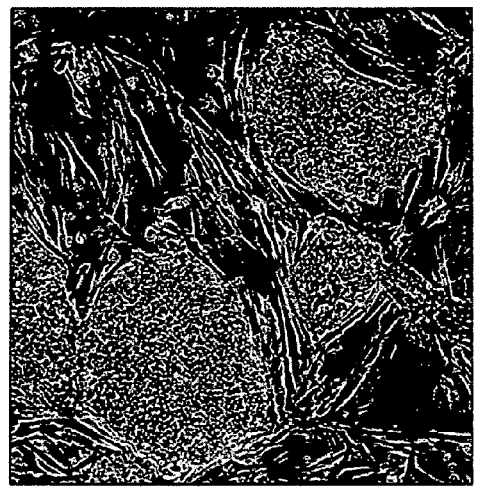

The present invention provides a method for producing human mast cells by induction of differentiation of human pluripotent stem cells using a medium supplemented with appropriate cytokines.

I. Pluripotent Stem Cells

In the present invention, "pluripotent stem cells" means cells maintaining their undifferentiated state/pluripotency, and examples thereof include embryonic stem cells (ES cells) and induced pluripotent stem cells (iPS cells). ES cells may be produced by reprogramming of nuclei of somatic cells. Examples of pluripotent stem cells other than ES cells include Embryonic Germ Cells (EG cells) derived from primordial germ cells, multipotent germline stem cells (mGS cells) isolated from testis, and Multipotent adult progenitor cells (MAPCs) isolated from bone marrow. In the present invention, these pluripotent stem cells are derived from human. In the present invention, the pluripotent stem cells are preferably iPS cells.

The method for producing iPS cells is described below.

II. A Method for Producing iPS Cells (A) Somatic Cell Sources

Somatic cells which can be used as starting materials for preparation of iPS cells may be any cells other than germ cells derived from human, and examples of the somatic cells include epithelial cells which are keratinized (e.g., keratinized epidermal cells), mucosal epithelial cells (e.g., epithelial cells of the lingual surface), epithelial cells of exocrine glands (e.g., mammary cells), hormone-secreting cells (e.g., adrenomedullary cells), cells for metabolism and storage (e.g., hepatic cells), luminal epithelial cells constituting boundary surfaces (e.g., type I alveolar cells), luminal epithelial cells in the closed circulatory system (e.g., vascular endothelial cells), ciliated cells having a carrying capacity (e.g., tracheal epithelial cells), extracellular matrix-secreting cells (e.g., fibroblasts), contractile cells (e.g., smooth muscle cells), cells involved in the blood system and the immune system (e.g., T lymphocytes), sensory cells (e.g., rod cells), autonomic neurons (e.g., cholinergic neurons), supporting cells of sense organs and peripheral neurons (e.g., satellite cells), nerve cells and glial cells in the central nervous system (e.g., astroglial cells) and pigment cells (e.g., retinal pigment epithelial cells), and progenitor cells (tissue progenitor cells) thereof. The level of differentiation of the cells and the age of the human from which the cells are collected are not restricted, and either undifferentiated progenitor cells (including somatic stem cell) or terminally-differentiated mature cells may be used in a similar manner as the source of the somatic cells. Here, examples of the undifferentiated progenitor cells include tissue stem cells (somatic stem cells) such as neural stem cells, hematopoietic stem cells, mesenchymal stem cells and dental pulp stem cells.

When the iPS cells are used as the source of cells for evaluation of drug sensitivity of a patient or the risk of side effects, it is preferred to collect somatic cells from the patient himself or another person who has the same genotypes which are related to the drug sensitivity or the side effects.

The somatic cells separated from human may be precultured, before providing them for the nuclear reprogramming step, in a per se known culture medium suitable for culture of the cells, depending on the type of the cells. Examples of the culture medium include, but are not limited to, minimum essential medium (MEM) supplemented with about 5 to 20% fetal bovine serum, Dulbecco's modified Eagle's medium (DMEM), RPMI1640 medium, 199 medium and F12 medium. When a gene transfer reagent such as cationic liposome is used upon contacting the cells with a nuclear reprogramming gene(s) and an inhibitor of the function of p53 (and, as required, another substance for improvement of the establishment efficiency of iPS cells), the culture medium may be preferably replaced with a serum-free medium to prevent decrease in the gene transfer efficiency.

(B) Nuclear Reprogramming Substances

In the present invention, the "nuclear reprogramming substance" may be a protein factor with which iPS cells can be induced from somatic cells, or a nucleic acid (including the nucleic acid incorporated in a vector) encoding the factor. The nuclear reprogramming substances used in the present invention may be those described in WO 2007/069666. More particular examples thereof include Oct3/4, Klf4, Klf1, Klf2, Klf5, Sox2, Sox1, Sox3, Sox15, Sox17, Sox18, c-Myc, L-Myc, N-Myc, TERT, SV40 Large T antigen, HPV16 E6, HPV16 E7, Bmi1, Lin28, Lin28b, Nanog, Esrrb and Esrrg. When iPS cells are established, these reprogramming substances may be used in combination, and the combination may include at least 1, 2 or 3, preferably 4, of the above reprogramming genes. More particular examples of the combination include the following combinations (only the names of protein factors are described below).

(1) Oct3/4, Klf4, Sox2, c-Myc (here, Sox2 can be replaced with Sox1, Sox3, Sox15, Sox17 or Sox18. Klf4 can be replaced with Klf1, Klf2 or Klf5. Further, c-Myc can be replaced with L-Myc or N-Myc.)
(2) Oct3/4, Klf4, Sox2, c-Myc, TERT, SV40 Large T antigen (hereinafter referred to as SV40LT)
(3) Oct3/4, Klf4, Sox2, c-Myc, TERT, HPV16 E6
(4) Oct3/4, Klf4, Sox2, c-Myc, TERT, HPV16 E7
(5) Oct3/4, Klf4, Sox2, c-Myc, TERT, HPV6 E6, HPV16 E7
(6) Oct3/4, Klf4, Sox2, c-Myc, TERT, Bmi1
(7) Oct3/4, Klf4, Sox2, c-Myc, Lin28
(8) Oct3/4, Klf4, Sox2, c-Myc, Lin28, SV40LT
(9) Oct3/4, Klf4, Sox2, c-Myc, Lin28, TERT, SV40LT
(10) Oct3/4, Klf4, Sox2, c-Myc, SV40LT
(11) Oct3/4, Esrrb, Sox2, c-Myc (Esrrb can be replaced with Esrrg.)
(12) Oct3/4, Klf4, Sox2
(13) Oct3/4, Klf4, Sox2, TERT, SV40LT
(14) Oct3/4, Klf4, Sox2, TERT, HPV16 E6
(15) Oct3/4, Klf4, Sox2, TERT, HPV16 E7
(16) Oct3/4, Klf4, Sox2, TERT, HPV6 E6, HPV16 E7
(17) Oct3/4, Klf4, Sox2, TERT, Bmi1
(18) Oct3/4, Klf4, Sox2, Lin28
(19) Oct3/4, Klf4, Sox2, Lin28, SV40LT
(20) Oct3/4, Klf4, Sox2, Lin28, TERT, SV40LT
(21) Oct3/4, Klf4, Sox2, SV40LT
(22) Oct3/4, Esrrb, Sox2 (Esrrb can be replaced with Esrrg.)

In the above list, Lin28b can be used instead of Lin28.

Further, although not included in the above-described (1) to (22), combinations that comprise, in addition to all the constituents in any of these, another arbitrary substance are also included within the scope of the "nuclear reprogramming substances". Further, under conditions where the somatic cells to be subjected to nuclear reprogramming are endogenously expressing a part of the constituents of any of the above (1) to (22) to a level(s) sufficient for nuclear reprogramming, the combination comprising the constituents other than endogenously expressed substances may be encompassed in the scope of the "nuclear reprogramming substance(s)" in the present invention.

Preferred examples of the combination of nuclear reprogramming factors, among these combinations, include the combination of the 4 factors, that is, Oct3/4, Sox2, Klf4 and c-Myc; and the combination of the 3 factors, that is, Oct3/4, Sox2 and Klf4. The combinations of the 5 or 4 factors including SV40 Large T antigen in addition to the 3 or 4 factors are also preferred.

The sequence information of human cDNAs of the above-described nuclear reprogramming substances may be obtained by reference to the NCBI (National Center for Biotechnology Information) accession numbers described in WO 2007/069666, and those skilled in the art can easily isolate these cDNAs. Examples of the sequence information of human cDNAs of Oct3/4, Sox2, Klf4, c-Myc, Lin28, Lin28b, Esrrb and Esrrg include the followings: Oct3/4 (NM_002701), Sox2 (NM_003106), Klf4 (NM_004235), c-Myc (NM_002467), Lin28 (NM_024674), Lin28b (NM_001004317), Esrrb (NM_004452) and Esrrg (NM_001438).

When a protein factor itself is used as a nuclear reprogramming substance, the protein factor can be prepared by inserting a cDNA encoding the factor into an appropriate expression vector and introducing the resulting vector into host cells, culturing the host cells, and recovering the recombinant protein factor. On the other hand, when a nucleic acid encoding a protein factor is used as a nuclear reprogramming substance, the cDNA is inserted into a virus vector, plasmid vector, episomal vector or the like to construct an expression vector, which is used in the nuclear reprogramming step.

(C) Method for Introducing a Nuclear Reprogramming Substance to Somatic Cells

The nuclear reprogramming substance can be introduced to somatic cells by, when the substance is a protein factor, using a per se known method for introduction of a protein to the cell. Examples of such a method include methods using a protein transduction reagent, methods using a protein transduction domain (PTD) or cell-penetrating peptide (CPP) fusion protein, and the microinjection method. Examples of the protein transduction reagent which are commercially available include cationic lipid-based BioPORTER Protein Delivery Reagent (Gene Therapy Systems), ProJect™ Protein Transfection Reagent (PIERCE) and ProVectin (IMGENEX); lipid-based Profect-1 (Targeting Systems); membrane-permeable-peptide-based Penetratin Peptide (Q biogene) and Chariot Kit (Active Motif); and GenomONE (Ishihara Sangyo Kaisha, Ltd.) which uses the HVJ envelope (inactivated Sendai virus). The introduction can be carried out according to the protocols attached to these reagents, and, in general, it may be carried out as follows. A nuclear reprogramming substance is diluted in an appropriate solvent (e.g., a buffer such as PBS or HEPES), and a transduction reagent is added to the resulting diluent, followed by incubation of the resulting mixture at room temperature for 5 to 15 minutes to allow formation of a complex, which is then added to the cells in a serum-free medium, and the resultant is incubated at 37° C. for 1 to several hours. Thereafter, the medium is removed and replaced with a serum-containing medium.

Examples of the PTD include ones developed using transcellular domains of proteins such as *Drosophila*-derived AntP, HIV-derived TAT (Frankel, A. et al, *Cell* 55, 1189-93 (1988); Green, M. & Loewenstein, P. M. *Cell* 55, 1179-88 (1988)), Penetratin (Derossi, D. et al, *J. Biol. Chem.* 269, 10444-50 (1994)), Buforin II (Park, C. B. et al. *Proc. Natl Acad. Sci. USA* 97, 8245-50 (2000)), Transportan (Pooga, M. et al. *FASEB J.* 12, 67-77 (1998)), MAP (model amphipathic peptide) (Oehlke, J. et al. *Biochim. Biophys. Acta.* 1414, 127-39 (1998)), K-FGF (Lin, Y. Z. et al. *J. Biol. Chem.* 270, 14255-14258 (1995)), Ku70 (Sawada, M. et al. *Nature Cell*

Biol. 5, 352-7 (2003)), Prion (Lundberg, P. et al. *Biochem. Biophys. Res. Commun.* 299, 85-90 (2002)), pVEC (Elmquist, A. et al. *Exp. Cell Res.* 269, 237-44 (2001)), Pep-1 (Morris, M. C. et al. *Nature Biotechnol.* 19, 1173-6 (2001)), Pep-7 (Gao, C. et al. *Bioorg. Med. Chem.* 10, 4057-65 (2002)), SynB1 (Rousselle, C. et al. *Mol. Pharmacol.* 57, 679-86 (2000)), HN-I (Hong, F. D. & Clayman, G L. *Cancer Res.* 60, 6551-6 (2000)) and HSV-derived VP22. Examples of the CPP derived from PTD include polyarginines such as 11R (*Cell Stem Cell*, 4:381-384 (2009)) and 9R (*Cell Stem Cell*, 4:472-476 (2009)).

A fusion protein expression vector in which cDNA of a nuclear reprogramming substance and a PTD or CPP sequence are incorporated is prepared to express recombinant fusion protein, followed by recovering the fusion protein to be used for the introduction. The introduction can be carried out in the same manner as described above except that a protein transduction reagent is not added.

Microinjection is a method wherein a protein solution is placed in a glass needle having a tip diameter of about 1 μm, followed by puncture introduction of the solution to a cell. Thereby, the protein can be surely introduced into the cell.

The operation of introduction of the protein can be carried out an arbitrary number of times which is not less than 1 (e.g., 1 to 10 times, 1 to 5 times, or the like), and the introduction operation can be preferably repeated not less than 2 times (e.g., 3 or 4 times). When the introduction operation is repeated, it is carried out at intervals of, for example, 6 to 48 hours, preferably 12 to 24 hours.

When the establishment efficiency of iPS cells is important, each nuclear reprogramming substance is preferably used in the form of a nucleic acid encoding it, rather than the protein factor itself. The nucleic acid may be either DNA or RNA, or a DNA/RNA chimera, and the nucleic acid may be either double-stranded or single-stranded. The nucleic acid is preferably double-stranded DNA, especially cDNA.

The cDNA of the nuclear reprogramming substance is inserted into an appropriate expression vector having a promoter which can function in a somatic cell used as a host. Examples of the expression vector include virus vectors such as retroviruses, lentiviruses, adenoviruses, adeno-associated viruses, herpesviruses and Sendai virus; and animal cell expression plasmids (e.g., pA1-11, pXT1, pRc/CMV, pRc/RSV and pcDNAI/Neo).

The type of the vector to be used may be appropriately selected depending on the use of the obtained iPS cells. Examples of the vector include adenovirus vectors, plasmid vectors, adeno-associated virus vectors, retrovirus vectors, lentivirus vectors, Sendai virus vectors and episomal vectors.

Examples of the promoter used in the expression vector include the EF1α promoter, CAG promoter, SRα promoter, SV40 promoter, LTR promoter, CMV (cytomegalovirus) promoter, RSV (Rous sarcoma virus) promoter, MoMuLV (Moloney murine leukemia virus) LTR and HSV-TK (herpes simplex virus thymidine kinase) promoter. Among these, the EF1α promoter, CAG promoter, MoMuLV LTR, CMV promoter, SRα promoter and the like are preferred.

The expression vector may comprise, as desired, in addition to the promoter, an enhancer, a poly (A) addition signal, a selection marker gene, the SV40 replication origin and/or the like. Examples of the selection marker gene include the dihydrofolate reductase gene, neomycin resistance gene and puromycin resistance gene.

The nucleic acids (reprogramming genes) which are nuclear reprogramming substances may be separately incorporated into expression vectors, or 2 or more types, preferably 2 to 3 types of the nucleic acids may be incorporated in a single expression vector. When a retrovirus or lentivirus vector which shows a high gene transfer efficiency is used, separate vectors are preferably used, and when a plasmid, adenovirus or episomal vector or the like is used, a single vector is preferably used. Further, an expression vector to which 2 or more types of the genes have been incorporated and an expression vector to which only one gene has been incorporated may be used in combination.

Here, when a plurality of the reprogramming genes (e.g., 2 or more selected from Oct3/4, Sox2, Klf4 and c-Myc: preferably 2 or 3 genes) are incorporated in a single expression vector, these plurality of genes may be incorporated into the expression vector preferably via sequences which enable polycistronic expression of the genes. By using the sequences enabling the polycistronic expression, the plurality of genes incorporated in the single expression vector can be more efficiently expressed. Examples of the sequences which enable the polycistronic expression include the 2A sequence in foot and mouth disease virus (PLoS ONE3, e2532, 2008, *Stem Cells* 25, 1707, 2007) and the IRES sequence (U.S. Pat. No. 4,937,190 B). The 2A sequence may be preferably used.

The expression vector containing the reprogramming gene(s) can be introduced into the cells by a per se known method depending on the type of the vector. For example, in the case of a virus vector, a plasmid containing the nucleic acid is introduced to an appropriate packaging cell line (e.g., Plat-E cells) or a complementing cell line (e.g., 293 cells), and the virus produced in the culture supernatant is recovered, followed by infection of the virus to the cells by an appropriate method depending on the type of the virus vector. For example, specific methods using a retrovirus vector as the vector are disclosed in WO2007/69666; *Cell*, 126, 663-676 (2006); and *Cell*, 131, 861-872 (2007); and usage of a lentivirus vector as the vector is disclosed in *Science*, 318, 1917-1920 (2007). When the iPS cells are used as the source of regenerative medicine, expression (reactivation) of the reprogramming gene(s) may increase the risk of carcinogenesis in the tissue regenerated from differentiated cells derived from the iPS cells, so that the reprogramming gene(s) is/are preferably not incorporated into a chromosome(s) of the cells, and only transiently expressed. In this view, an adenovirus vector, which is rarely incorporated into a chromosome, is preferably used. A specific method for using an adenovirus vector is disclosed in *Science*, 322, 945-949 (2008). Further, since adeno-associated viruses also show low frequencies of incorporation into chromosomes, and show less cytotoxicities and less inflammatory actions compared to adenovirus vectors, they can be other examples of preferred vectors. Sendai virus vectors can stably extrachromosomally exist and can be degraded and removed by siRNAs as required, so that they may also be preferably used. Examples of the Sendai virus vectors include those described in *J. Biol. Chem.*, 282, 27383-27391 (2007) and JP 3602058 B.

When a retrovirus vector or a lentivirus vector is used, the introduced gene(s) may be reactivated even after their silencing, so that a method using the Cre/loxP system, in which the nucleic acid(s) encoding the nuclear reprogramming substance(s) is/are excised, is preferably used when the nucleic acid(s) became unnecessary. That is, the loxP sequences are arranged in the both ends of the nucleic acid(s), and, after induction of iPS cells, Cre recombinase is allowed to act on the cells using a plasmid vector or an adenovirus vector, thereby enabling excision of the region between the loxP sequences. Further, since the enhancer-promoter sequence in the LTR U3 region may upregulate a host gene in the vicinity thereof by insertional mutagenesis, it is preferred to avoid regulation of expression of an endogenous gene by the LTR outside the loxP sequence which has not been excised and remaining in the genome, by using a 3'-self-inactivating (SIN) LTR where the enhancer-promoter sequence is deleted or replaced with polyadenylation sequence derived from SV40 etc. A specific method using the Cre-loxP system and SIN LTR is disclosed in Chang et al., *Stem Cells,* 27: 1042-1049 (2009).

On the other hand, when the vector is a plasmid vector which is a nonviral vector, the vector can be introduced to the cells by using the lipofection method, liposome method, electroporation method, calcium phosphate coprecipitation method, DEAE-dextran method, microinjection method, gene gun method or the like. Particular examples of the method using a plasmid as the vector include ones described in *Science,* 322, 949-953 (2008) and the like.

When a plasmid vector, adenovirus vector or the like is used, the gene transfer can be carried out an arbitrary number of times which is not less than 1 (e.g., 1 to 10 times, 1 to 5 times, or the like). When not less than 2 types of expression vectors are introduced to somatic cells, all of these types of vectors are preferably introduced to the somatic cells at the same time, and also in such cases, operation of the gene transfer may be carried out an arbitrary number of times which is not less than 1 (e.g., 1 to 10 times, 1 to 5 times, or the like). The operation of gene transfer may be preferably repeated not less than 2 times (e.g., 3 or 4 times).

Since, when an adenovirus or a plasmid is used, the transgene(s) may be incorporated into a chromosome(s), it is eventually necessary to confirm that the gene(s) is/are not inserted into a chromosome(s), by Southern blotting and/or PCR. Therefore, it may be advantageous to use a method to remove the transgene(s) after incorporation thereof into a chromosome(s), such as the above-described Cre-loxP system. In another preferred mode, a method may be employed wherein, after incorporation of the transgene(s) into a chromosome(s) using a transposon, transposase is allowed to act on the cells using a plasmid vector or an adenovirus vector, thereby completely removing the transgene(s) from the chromosome(s). Preferred examples of the transposon include piggyBac, which is a transposon derived from a lepidopteran insect. Specific examples of the method using the piggyBac transposon include those disclosed in Kaji, K. et al., *Nature,* 458: 771-775 (2009) and Woltjen et al., *Nature,* 458: 766-770 (2009).

Another preferred non-incorporation type vector is an episomal vector, which can be extrachromosomally and autonomously replicated. Particular examples of the method using an episomal vector include the method disclosed in Yu et al., *Science,* 324, 797-801 (2009). In one preferred mode of the present invention, an expression vector is constructed by inserting a reprogramming gene(s) into an episomal vector wherein loxP sequences are arranged in the same direction in the 5'-side and the 3'-side of the vector elements required for replication of the episomal vector. By introducing the resulting vector to somatic cells, the vector existing as an episome drops from the iPS cells at an early stage without even transient incorporation of the exogenous nucleic acid factors constituting the vector (including the reprogramming gene(s)) into the genome of the cells.

Examples of the episomal vector include those having, as vector elements, sequences necessary for their autonomous replication, which are derived from EBV, SV40 or the like. More particularly, the vector elements necessary for autonomous replication are the replication origin and a gene encoding a protein that is bound to the replication origin to regulate the replication, and examples thereof include the replication origin oriP and the EBNA-1 gene in the case of EBV; and the replication origin ori and the SV40 large T antigen gene in the case of SV40.

Further, the episomal expression vector has a promoter that regulates transcription of the reprogramming gene. Examples of the promoter include those as described above. The episomal expression vector may further comprise, as desired, an enhancer, a poly (A) addition signal, a selection marker gene and/or the like, as described above. Examples of the selection marker gene include the dihydrofolate reductase gene and neomycin resistance gene.

The episomal vector can be introduced to the cells by using the lipofection method, liposome method, electroporation method, calcium phosphate coprecipitation method, DEAE-dextran method, microinjection method, gene gun method or the like. Specific examples of the method include those described in *Science,* 324, 797-801 (2009) and the like.

Whether or not the vector elements necessary for replication of the reprogramming gene(s) are removed from the iPS cells can be confirmed by Southern blot analysis or PCR analysis using, as a probe or a primer, a nucleic acid containing a sequence inside the vector elements and/or a sequence in the vicinity of the loxP sequence, and, as the template, the episome fraction isolated from the iPS cells, followed by investigation of presence or absence of a band or the length of the detected band. Preparation of the episome fraction may be carried out by a method well-known in the art, and examples of the method include ones described in *Science,* 324: 797-801 (2009) and the like.

(D) Inhibitors of the Function of p53

In addition to the nuclear reprogramming substance(s) described above, an inhibitor of the function of p53 is preferably brought into contact with the cells. The "inhibitor of the function of p53" may be any substance as long as it inhibits (a) the function of the p53 protein or (b) expression of the p53 gene. That is, the "inhibitor of the function of p53" is not restricted to a substance that directly acts on the p53 protein to inhibit its function and a substance that directly acts on the p53 gene to inhibit its expression, and also includes a substance that acts on a factor involved in signal transduction of p53 and thereby inhibits expression of the function of the p53 protein or expression of the p53 gene. The inhibitor of the function of p53 is preferably a substance which inhibits expression of the p53 gene, more preferably an expression vector encoding a siRNA or shRNA against p53.

Examples of the substance which inhibits the function of the p53 include, but are not limited to, chemical inhibitors of p53; dominant-negative mutants of p53 and nucleic acids encoding them; anti-p53 antagonistic antibodies and nucleic acids encoding them; decoy nucleic acids containing the consensus sequences of p53-response elements; and inhibitors of the p53 pathway. The substance is preferably a chemical inhibitor of p53; a dominant-negative mutant of p53 or a nucleic acid encoding it; or an inhibitor of the p53 pathway.

(D1) Chemical Inhibitors of p53

Examples of the chemical inhibitor of p53 include, but are not limited to, p53 inhibitors represented by pifithrin (PFT)-α and -β disclosed in WO 00/44364; and PFT-µ disclosed in Storm et al. (*Nat. Chem. Biol.* 2, 474 (2006)) and analogues and salts thereof (e.g., acid addition salts such as hydrochloric acid salt and bromate). Among these, PFT-α and analogues thereof [2-(2-Imino-4,5,6,7-tetrahydrobenzothiazol-3-yl)-1-p-tolylethanone, HBr (product name: Pifithrin-α) and 1-(4-Nitrophenyl)-2-(4,5,6,7-tetrahydro-2-imino-3(2H)-benzothiazolyl)ethanone, HBr (product name: Pifithrin-α, p-Nitro)]; PFT-β and analogues thereof [2-(4-Methylphenyl) imidazo[2,1-b]-5,6,7,8-tetrahydrobenzothiazole, HBr (product name: Pifithrin-α, Cyclic) and 2-(4-Nitrophenyl)imidazo[2,1-b]-5,6,7,8-tetrahydrobenzothiazole (product name: Pifithrin-α, p-Nitro, Cyclic)]; and PFT-μ [Phenylacetylenylsulfonamide (product name: Pifithrin-μ)] are commercially available from Merck.

The chemical inhibitor of p53 can be contacted with somatic cells by dissolving the inhibitor in an aqueous or nonaqueous solvent at an appropriate concentration, adding the resulting inhibitor solution to a medium suitable for culture of somatic cells isolated from human or mouse (e.g., minimum essential medium (MEM) supplemented with about 5 to 20% fetal bovine serum, Dulbecco's modified Eagle's medium (DMEM), RPMI1640 medium, 199 medium or F12 medium) to attain an inhibitor concentration within the range where the function of p53 is sufficiently inhibited and cytotoxicity is not observed, and culturing the cells for a certain period. The inhibitor concentration varies depending on the type of the inhibitor, and appropriately selected within the range of about 0.1 nM to about 100 nM. The contacting period is not restricted as long as it is sufficient for achievement of nuclear reprogramming of the cells, and, usually, the inhibitor may exist in the medium until appearance of positive colonies.

The p53 gene is known as a tumor suppressor gene, and therefore constant inhibition of the function of p53 may increase the risk of carcinogenesis. A chemical inhibitor of p53 is advantageous since it can be simply introduced to cells by addition thereof to the medium, and moreover, it is useful since the inhibition of the function of p53 can be simply and quickly canceled by removal of the medium containing the inhibitor after induction of iPS cells.

(D2) Dominant Negative Mutant of p53

The dominant negative mutant of p53 is not restricted as long as it acts competitively with the endogenous wild-type p53 protein in somatic cells and inhibits its function, and examples of the dominant negative mutant include p53P275S (de Vries, A., *Proc. Natl. Acad. Sci. USA*, 99, 2948-2953 (2002)) produced by changing the proline at position 275, which is positioned in the DNA binding region of murine p53 (position 278 in the case of human), to serine by point mutation; and p53DD (Bowman, T., *Genes Develop.*, 10, 826-835 (1996)) produced by deleting the amino acids at positions 14 to 301 of murine p53 (which corresponds to positions 11 to 304 in human p53). Other known examples of the dominant negative mutant which can be similarly used include p53S61A produced by changing the serine at position 61 of human p53 to alanine by point mutation, p53C135Y produced by changing the cysteine at position 135 of human p53 to tyrosine by point mutation, p53A138V produced by changing the alanine at position 138 of human p53 to valine by point mutation, p53R175H produced by changing the arginine at position 175 of human p53 to histidine by point mutation, p53R273H produced by changing the arginine at position 273 of human p53 to histidine by point mutation, and p53D281N produced by changing the aspartic acid at position 281 of human p53 to asparagine by point mutation.

A dominant negative mutant of p53 can be obtained by, for example, the following method. First, an appropriate oligonucleotide is synthesized based on the sequence information of human p53 cDNA as a probe or a primer, and mouse or human p53 cDNA is cloned from mRNAs, cDNAs or a cDNA library derived from cells or a tissue of mouse or human using the hybridization method or the (RT-)PCR method, followed by subcloning of the resulting clone into an appropriate plasmid. A primer containing the position to which the mutation is to be introduced is synthesized such that the codon of the position (for example, in the case of p53P275S, cct represented as base numbers 951 to 953 from the initiation codon) is replaced with a codon encoding another desired amino acid (for example, in the case of p53P275S, tct), which primer is then used for inverse PCR using as the template the plasmid into which the p53 cDNA was inserted, thereby obtaining a nucleic acid encoding the dominant negative mutant of interest. In the case of a deletion mutant such as p53DD, primers may be designed in the outside of the position to be deleted, and inverse PCR may be carried out in the same manner. By introducing the thus obtained nucleic acid encoding a dominant negative mutant to host cells and culturing the cells to obtain culture, followed by recovery of a recombinant protein therefrom, the dominant negative mutant of interest can be obtained.

The dominant negative mutant can be contacted with somatic cells in the same manner as in the case of the above-described protein nuclear reprogramming substance. As mentioned above, constant inhibition of the function of p53 may increase the risk of carcinogenesis, but the dominant negative mutant of p53 gradually disappears by degradation by proteases in the cells into which it was introduced, and the function of endogenous p53 in the cells is recovered accordingly, so that use of the mutant protein may be suitable when a high level of safety is required, such as in cases where the obtained iPS cells are used for therapy.

(D3) A Nucleic Acid Encoding a Dominant Negative Mutant of p53

In another preferred mode of the present invention, the inhibitor of the function of p53 is a nucleic acid encoding a dominant negative mutant of p53. The nucleic acid may be either DNA or RNA, or a DNA/RNA chimera, and it is preferably DNA. The nucleic acid may be either double-stranded or single-stranded. The cDNA encoding a dominant negative mutant of p53 can be cloned by the method described above for preparation of the mutant protein.

The isolated cDNA can be inserted into an appropriate expression vector and introduced to somatic cells, as in the case of the nucleic acid encoding the nuclear reprogramming substance (reprogramming gene).

(D4) p53 Pathway Inhibitor

Here, the term "p53 pathway" means any upstream signal cascade that may activate p53, as well as any downstream signal cascade mediated by activated p53. Therefore, any substance that inhibits any of the above-described signal transduction pathways is included in the p53 pathway inhibitor. In one preferred mode, the p53 pathway inhibitor is a substance that inhibits expression or the function (Myc inhibition action) of p21 whose expression is activated by p53, such as a siRNA, shRNA, antisense nucleic acid or ribozyme against p21. These nucleic acids that inhibit expression of p21 can be designed/synthesized in the same manner as siRNAs, shRNAs, antisense nucleic acids and ribozymes against p53 as described later, and introduced to somatic cells. The nucleic acids may be provided in the forms of vectors which express them, and the vectors can be constructed in the same manner as vectors that express siRNAs, shRNAs, antisense nucleic acids and ribozymes against p53 as described later, and introduced to somatic cells.

In another preferred mode, the p53 pathway inhibitor is a substance that inhibits the ARF-MDM2-p53 pathway, and examples of the ARF-MDM2-p53 pathway inhibitor include MDM2 that is directly bound to p53 and thereby promote its nuclear export and ubiquitination, and nucleic acids encoding MDM2; and substances that inhibit expression or the functions of p19$^{ARF}$ and ATM (ataxia-telangiectasia mutated) that inhibit the action of MDM2 on p53 (for example, siRNAs and shRNAs against these factors).

(D5) Other Substances

Examples of other substances that inhibit the function of the p53 protein include anti-p53 antagonistic antibodies and nucleic acids encoding them. The anti-p53 antagonistic antibody may be either a polyclonal antibody or a monoclonal antibody. The isotype of the antibody is not restricted, and preferably IgG, IgM or IgA, especially preferably IgG. The antibody may also be in the form of, for example, in addition to a complete antibody molecule, a fragment such as Fab, Fab', F(ab')$_2$ or the like; or a conjugate molecule prepared by genetic engineering, such as scFv, scFv-Fc, minibody or diabody; or a derivative thereof modified with a molecule having a protein stabilization action, such as polyethylene glycol (PEG), or the like. The anti-p53 antagonistic antibody can be produced according to a per se known production method for antibodies or antisera, by using p53 or its partial peptide as an antigen. Examples of known anti-p53 antagonistic antibodies include PAb1801 (Oncogene Science Ab-2) and DO-1 (Oncogene Science Ab-6) (Gire and Wynford-Thomas, *Mol. Cell. Biol.*, 18, 1611-1621 (1998)). A nucleic acid encoding an anti-p53 antagonistic antibody can be isolated by a conventional method from an anti-p53 monoclonal antibody-producing hybridoma. It is also possible to prepare a nucleic acid encoding a single-chain antibody by linking the obtained H-chain and L-chain genes together.

Examples of other substances that inhibit the function of the p53 protein include anti-p21 antagonistic antibodies and nucleic acids encoding them. Anti-p21 antagonistic antibodies and nucleic acids encoding them can be prepared in the same manner as the above-described p53 antagonistic antibodies and nucleic acids encoding them.

Further examples of other substances that inhibit the function of the p53 protein include decoy nucleic acids containing the consensus sequences of p53-response elements (e.g., Pu-Pu-Pu-G-A/T-T/A-C-Py-Py-Py (Pu: purine base, Py: pyrimidine base)). Such nucleic acids can be synthesized by a DNA/RNA synthesizer based on the above-described base sequence information. Such decoy nucleic acids are also commercially available (e.g., p53 transcription factor decoy (GeneDetect.com)).

Anti-p53 antagonistic antibodies and anti-p21 antagonistic antibodies can be introduced to cells in the same manner as the dominant negative mutants of p53, and nucleic acids encoding the antibodies can be introduced to cells in the same manner as the nucleic acids encoding the mutants. Further, the above decoy nucleic acids can be introduced to cells by the lipofection method or the like.

On the other hand, examples of the substance that inhibits expression of the p53 gene include siRNAs and shRNAs against p53; vectors that express siRNAs and shRNAs against p53; antisense nucleic acids against p53; and ribozymes against p53; and the substance that inhibits expression of the p53 gene is preferably a siRNA or a shRNA, or a vector that expresses a siRNA or a shRNA.

(D6) siRNAs and shRNAs against p53

A siRNA against p53 can be designed based on the sequence information of human p53 cDNA (NCBI No. NM_000546), according to, for example, the theory proposed by Elbashir et al. (*Genes Dev.*, 15, 188-200 (2001)). The target sequence of the siRNA is essentially AA+(N)19, and it may also be AA+(N)21 or NA+(N)21. The 5'-end of the sense strand does not need to be AA. The position of the target sequence is not restricted, and it is preferred to select a target sequence from the region other than 5'-UTR, the region corresponding to about 50 bases from the initiation codon, and 3'-UTR. The GC content of the target sequence is also not restricted, and it is preferably about 30% to about 50%. The target sequence preferably has an unbiased GC distribution and less repetition. When a pol III promoter is used as the promoter when a vector that expresses a siRNA or a shRNA described in (b2) below is designed, a sequence containing not less than 4 continuous Ts or As should be avoided in order not to stop transcription by polymerase.

The candidates of the target sequence selected based on the above-described theory are checked in terms of whether they do not show homologies to sequences of continuous 16 to 17 bases in mRNAs other than the target, using a homology search software such as BLAST (http://www.ncbi.nlm.nih.gov/BLAST/), to confirm specificities of the selected target sequences. For each target sequence whose specificity was confirmed, a double-stranded DNA is designed as a siRNA, which double-stranded DNA consists of a sense strand having 19 to 21 bases after the AA (or NA), followed by the 3'-end overhang of TT or UU, and an antisense strand having the sequence complementary to the 19 to 21 bases, followed by the 3'-end overhang of TT or UU. A shRNA can be designed by appropriately selecting an arbitrary linker sequence (e.g., about 8 to about 25 bases in length) that can form a loop structure and linking the above-described sense strand and antisense strand via the linker sequence.

Sequences of siRNAs and/or shRNAs can be searched using search engines freely available in various websites. Examples of such sites include, but are not limited to, siRNA Target Finder (http://www.ambion.com/jp/techlib/misc/siRNA_finder.html) and Insert Design Tool for the pSilencer™ Expression Vectors (http://www.ambion.com/jp/techlib/misc/psilencer_converter.html) provided by Ambion; and GeneSeer (http://codex.cshl.edu/scripts/newsearchhairpin.cgi) provided by RNAi Codex; and similar search can be carried out also on the websites of QIAGEN, Takara Bio, SiSearch, Dharmacon, Whitehead Institute, Invitrogen, Promega and the like.

A siRNA against p53 can be prepared by a process wherein the thus designed respective oligonucleotides of the sense strand and the antisense strand are synthesized by a DNA/RNA synthesizer and denatured in, for example, an appropriate annealing buffer at about 90° C. to about 95° C. for about 1 minute, followed by annealing at about 30° C. to about 70° C. for about 1 to about 8 hours. A shRNA against p53 can be prepared by synthesizing an oligonucleotide having a shRNA sequence designed as described above in a DNA/RNA synthesizer, and allowing its self-annealing in the same manner as described above.

The nucleotide molecule constituting the siRNA or the shRNA may either be a wild-type RNA or have various chemical modifications in order to enhance the stability (chemical and/or anti-enzyme) and the specific activity (affinity to mRNA). For example, in order to prevent degradation by hydrolases such as nuclease, the phosphate residue (phosphate) of each nucleotide constituting the antisense nucleic acid may be substituted with a chemically modified phosphate residue such as phosphorothioate (PS), methylphosphonate or phosphorodithionate. Further, the hydroxyl group at 2'-position of the sugar (ribose) of each nucleotide may be substituted with —OR (wherein R represents $CH_3$(2'-O-Me), $CH_2CH_2OCH_3$(2'-O-MOE), $CH_2CH_2NHC(NH)NH_2$, $CH_2CONHCH_3$, $CH_2CH_2CN$ or the like). Further, the base moiety (pyrimidine or purine) may be chemically modified, and examples of the chemical modification include introduction of a methyl group or a cationic functional group to 5-position of a pyrimidine base and substitution of the carbonyl group at 2-position to thiocarbonyl.

As conformations of the sugar moiety of the RNA, C2'-endo (S type) and C3'-endo (N type) are predominant. In the case of a single-stranded RNA, the both exist in equilibrium, but when a double strand is formed, the conformation is fixed to the N type. Therefore, BNA (LNA) (Iinanishi, T. et al., *Chem. Commun.*, 1653-9, 2002; Jepsen, J. S. et al., *Oligonucleotides*, 14, 130-46, 2004) and ENA (Morita, K. et al., *Nucleosides Nucleotides Nucleic Acids*, 22, 1619-21, 2003), which are RNA derivatives produced by cross-linking the 2' oxygen and the 4' carbon together to fix the conformation of the sugar moiety to the N type in order to give a strong binding capacity to the target RNA, are also preferably used.

However, since, when all the ribonucleoside molecules in a wild-type RNA are substituted with a modified type, the RNAi activity may be lost, introduction of modified nucleosides should be minimal in order to allow the RISC complex to function.

The siRNA against p53 may also be purchased from, for example, Ambion (e.g., Ambion Cat# AM16708, siRNA ID#69659, 69753, 69843, 187424, 187425 and 187426) or Santa Cruz (e.g., Santa Cruz Cat# sc-29436 and 44219).

Further, siRNAs and shRNAs against human p53 may also be designed using any of the search engines described above by inputting as a query the human p53 cDNA sequence (NCBI No. NM_000546) or the like, and synthesized; or purchased from Ambion or the like. Particular examples of the siRNAs and shRNAs against human p53 include the shRNA against p53 described in *Science*, 296, 550-553 (2002).

The siRNA or shRNA against p53 may be brought into contact with somatic cells by, in the same manner as in the case of a plasmid DNA, introducing the nucleic acid into the cells by using the liposome method, polyamine method, electroporation method, bead method or the like. The method using cationic liposome is most commonly used and shows high transfer efficiency. In addition to common gene transfer reagents such as Lipofectamine2000 and Oligofectamine (Invitrogen), transfer reagents suitable for siRNA transfer such as GeneEraser™ siRNA transfection reagent (Stratagene) are commercially available.

(D7) A Vector that Expresses a siRNA or shRNA Against p53

Vectors which express siRNAs can be grouped into the tandem type and the stem-loop (hairpin) type. In the former type, an expression cassette for the sense strand of a siRNA and an expression cassette for the antisense strand of the siRNA are tandemly linked, and a double-stranded siRNA (dsRNA) is formed by expression and annealing of the both strands in the cell. On the other hand, in the latter type, an expression cassette of a shRNA is inserted into a vector, and the shRNA is expressed in the cell and processed by Dicer to form a dsRNA. Examples of the promoter include pol II promoters (e.g., the CMV immediate-early promoter), but a pol III promoter is commonly used for accurate transcription of a short RNA. Examples of the pol III promoter include the murine and human U6-snRNA promoters, the human H1-RNase P RNA promoter and the human valine-tRNA promoter. As a transcription termination signal, a sequence having not less than 4 consecutive "T"s is used.

The thus constructed siRNA or shRNA expression cassette is then inserted into a plasmid vector or a virus vector. As such a vector, those described above for the nucleic acid encoding the nuclear reprogramming substance (reprogramming gene) may be preferably used (examples thereof include virus vectors such as retroviruses, lentiviruses, adenoviruses, adeno-associated viruses, herpesviruses and Sendai virus; animal cell expression plasmids; episomal vectors; and the like). The vector may be appropriately selected depending on the use of the obtained iPS cells, as in the case of the nuclear reprogramming gene. Alternatively, as the expression vector encoding a shRNA against p53, a virus vector such as a retrovirus; a plasmid vector; or an episomal vector; prepared based on a commercially available plasmid (e.g., pMKO.1-puro p53 shRNA2: #10672 commercially available from Addgene, or the like) may also be used. As required, the above-described Cre-loxP system or the piggyBac transposon system may also be used.

The vector that expresses a siRNA or shRNA against p53 is brought into contact with somatic cells by introducing the plasmid vector, episomal vector or virus vector prepared as described above into the cells. This gene transfer can be carried out by the same method as described above for the reprogramming gene.

(D8) Other Substances

Examples of other substances that inhibit expression of the p53 gene include antisense nucleic acids and ribozymes against p53.

The antisense nucleic acid may be either DNA or RNA, or a DNA/RNA chimera. When the antisense nucleic acid is DNA, the RNA:DNA hybrid formed by the target RNA and the antisense DNA can be recognized by endogenous RNase H to cause selective degradation of the target RNA. Therefore, in the case of an antisense DNA directed to degradation by RNase H, the target sequence may be, in addition to a sequence in p53 mRNA, a sequence in an intron region in the early transcription product of p53. The length of the target region in the antisense nucleic acid is not restricted as long as translation to the p53 protein is inhibited as a result of hybridization of the antisense nucleic acid to the target region. The target region may be either the total sequence or a partial sequence of p53 mRNA, and from a sequence having a length of about 15 bases to the entire sequence of the mRNA or the early transcription product. In consideration of simplicity of synthesis, antigenicity, and ability of transfer into the cell, the antisense nucleic acid is preferably an oligonucleotide having a length of preferably about 15 to about 40 bases, especially preferably about 18 to about 30 bases. Examples of the position of the target sequence include, but are not limited to, 5'- and 3'-UTR, and the vicinity of the initiation codon.

The term "ribozyme" means, in the narrow sense, RNA having an enzymatic activity of cleaving a nucleic acid, but, in the present specification, it is used as a concept including also DNA as long as it has a nucleic acid-cleaving activity that is sequence-specific. The most versatile examples of ribozymes include self-splicing RNAs observed in infectious RNAs such as viroids and virusoids, wherein the hammerhead type, hairpin type and the like are known. The hammerhead type has a length of about 40 bases, and exerts its enzymatic activity to specifically cleave a target mRNA when it is designed such that the sequences of the both ends having lengths of several bases (about 10 bases in total) adjacent to the portion forming a hammer head structure are complementary to the desired cleavage site in the mRNA.

The antisense nucleic acid and the ribozyme can be synthesized using a DNA/RNA synthesizer. The nucleotide molecules constituting these may have the same modifications as those in the case of the above-described siRNA, to enhance the stability and the specific activity.

Alternatively, the antisense nucleic acid and the ribozyme can be used in the forms of nucleic acids encoding them, as in the case of the siRNA.

The inhibitor of the function of p53 needs to be brought into contact with somatic cells in a manner sufficient for inhibition of the function of p53 during the nuclear reprogramming process of the somatic cells. As long as this condition is satisfied, the nuclear reprogramming substance(s) and the inhibitor of the function of p53 may be brought into contact with the somatic cells at the same time, or one of these may be first brought into contact therewith. In one mode, when, for example, the nuclear reprogramming substance(s) is/are a nucleic acid(s) encoding a protein factor(s) and the inhibitor of the function of p53 is a chemical inhibitor, there is a certain period of lag before abundant expression of the protein factor, while the chemical inhibitor exerts rapid inhibition of the function of p53, so that the chemical inhibitor of p53 may be added to the medium a certain period after the gene transfer process. In another mode, when, for example, the nuclear reprogramming substance(s) and the inhibitor of the function of p53 are both used in the form(s) of a virus vector, plasmid vector, episomal vector and/or the like, the both may be introduced to the cells at the same time.

(E) Substances for Improvement of the Establishment Efficiency of iPS Cells

The establishment efficiency of iPS cells is expected to be further enhanced by bringing, in addition to the above nuclear reprogramming factor(s) and the like, another/other known substance(s) for improvement of the establishment efficiency of iPS cells into contact with somatic cells. Examples of such a substance(s) for improvement of the establishment efficiency of iPS cells include, but are not limited to, histone deacetylase (HDAC) inhibitors [e.g., low molecular inhibitors such as valproic acid (VPA) (*Nat. Biotechnol.*, 26(7): 795-797 (2008)), trichostatin A, sodium butyrate, MC 1293 and M344; and nucleic acid-based expression inhibitors such as siRNAs and shRNAs against HDAC (e.g., HDAC1 siRNA Smartpool® (Millipore) and HuSH 29 mer shRNA Constructs against HDAC1 (OriGene)) and the like]; G9a histone methyltransferase inhibitors [e.g., low molecular inhibitors such as BIX-01294 (*Cell Stem Cell,* 2: 525-528 (2008)); and nucleic acid-based expression inhibitors such as siRNAs and shRNAs against G9a (e.g., G9a siRNA (human) (Santa Cruz Biotechnology))]; L-calcium channel agonists (e.g., Bayk8644) (*Cell Stem Cell,* 3, 568-574 (2008)); UTF1 (*Cell Stem Cell,* 3, 475-479 (2008)); Wnt Signaling (e.g., soluble Wnt3a) (*Cell Stem Cell,* 3, 132-135 (2008)); 2i/LIF (2i is an inhibitor of mitogen-activated protein kinase signaling and glycogen synthase kinase-3, *PLoS Biology,* 6(10), 2237-2247 (2008)); and ES cell-specific miRNAs [e.g., miR-302-367 cluster (*Mol. Cell. Biol. doi:*10.1128/MCB.00398-08 and WO2009/075119), miR-302 (RNA (2008) 14: 1-10), and miR-291-3p, miR-294 and miR-295 (these are described in *Nat. Biotechnol.* 27: 459-461 (2009))]. In the above examples, the nucleic acid-based expression inhibitors may be in the forms of expression vectors containing DNAs encoding siRNAs and shRNAs.

Among the constituents of the nuclear reprogramming substance(s), SV40 large T and the like may be included within the scope of the substances for improvement of the establishment efficiency of iPS cells in view of the fact that they are not indispensable for nuclear reprogramming of somatic cells and therefore auxiliary factors. Currently, the mechanism of nuclear reprogramming is unknown, so that auxiliary factors which are not indispensable for nuclear reprogramming may be positioned, for convenience, either as nuclear reprogramming factors or substances for improvement of the establishment efficiency of iPS cells. That is, the process of nuclear reprogramming of somatic cells can be understood, as a whole, a phenomenon caused by contacting of the nuclear reprogramming substance(s) and the substance(s) for improvement of the establishment efficiency of iPS cells with somatic cells, so that those skilled in the art would not need to distinguish between these.

These other substances for improvement of the establishment efficiency of iPS cells can be brought into contact with somatic cells in the same manner as described above for the inhibitor of the function of p53, depending on the type of the substances, that is, (a) a protein factor; (b) a nucleic acid encoding the protein factor; or (c) a low molecular compound.

The other substances for improvement of the establishment efficiency of iPS cells may be brought into contact with somatic cells at the same time with the nuclear reprogramming substance(s), or one of these may be first brought into contact therewith as long as the establish efficiency of iPS cells from somatic cells is improved significantly as compared to the case without the substance. Thus, the timing of the contact with somatic cells may be the same as described above for the inhibitor of the function of p53, depending on the physical properties of the substances.

(F) Improvement of the Establishment Efficiency by the Culture Conditions

The establishment efficiency of iPS cells can be further improved by culturing the cells under hypoxic condition during the process of nuclear reprogramming of somatic cells. Here, the term "hypoxic condition" means that the oxygen concentration in the atmosphere during the culture of the cells is significantly lower than that in the air. Particular examples of the condition include those where the oxygen concentration is lower than the oxygen concentration in the atmosphere of a 5 to 10% $CO_2$/95 to 90% air, and a condition where the oxygen concentration in the atmosphere is not more than 18% is included in such examples. The oxygen concentration in the atmosphere is preferably less than 15% (e.g., less than 14%, less than 13%, less than 12% or less than 11%), less than 10% (e.g., less than 9%, less than 8%, less than 7% or less than 6%), or less than 5% (e.g., less than 4%, less than 3% or less than 2%). Further, the oxygen concentration in the atmosphere is preferably more than 0.1% (e.g., more than 0.2%, more than 0.3% or more than 0.4%), more than 0.5% (e.g., more than 0.6%, more than 0.7%, more than 0.8% or more than 0.95%), or more than 1% (e.g., more than 1.1%, more than 1.2%, more than 1.3% or more than 1.4%).

The method for creating a hypoxic state in the cellular environment is not restricted, and the simplest and preferred examples thereof include a method wherein the cells are cultured in a $CO_2$ incubator in which the oxygen concentration can be controlled. The $CO_2$ incubator with which the oxygen concentration can be controlled is commercially available from various equipment manufacturers (for example, $CO_2$ incubators for hypoxic culture produced by manufacturers such as Thermo scientific, Ikemoto Scientific Technology Co., Ltd., Juji Field Inc. and Wakenyaku Co., Ltd. may be used).

The timing of initiation of the cell culture under hypoxic condition is not restricted as long as the improvement of the establishment efficiency of iPS cells relative to the establishment efficiency in the case of a normal oxygen concentration (20%) is not prevented, and may be before, during, or after the contact with the nuclear reprogramming substance(s). For example, the culturing under hypoxic condition is preferably carried out immediately, or after a certain period (for example, 1 to 10 (2, 3, 4, 5, 6, 7, 8 or 9) days), after the contact with the nuclear reprogramming substance(s).

The length of time of the culture of cells under hypoxic condition is not restricted as long as the improvement of the establishment efficiency of iPS cells relative to the establishment efficiency in the case of a normal oxygen concentration (20%) is not prevented, and examples of the length of time include, but are not limited to, not less than 3 days, not less than 5 days, not less than 7 days or not less than 10 days, and not more than 50 days, not more than 40 days, not more than 35 days or not more than 30 days. The preferred length of time of the culture under hypoxic condition varies depending on the oxygen concentration in the atmosphere, and those skilled in the art may appropriately control the culturing time depending on the oxygen concentration employed. Further, in one mode, when candidate colonies of iPS cells are selected using drug resistance as an index, the cells are preferably returned from the hypoxic condition to a condition where the oxygen concentration is normal.

Further, preferred timing of initiation of the cell culture under hypoxic condition and a preferred length of time of the culture vary depending on the type(s) of the nuclear reprogramming substance(s) employed and the establishment efficiency of iPS cells under a condition where the oxygen concentration is normal.

After contacting the nuclear reprogramming substance(s) and the inhibitor of the function of p53 (and, as required, other substance(s) for improvement of the establishment efficiency of iPS cells) with the cells, the cells may be cultured, for example, under conditions suitable for culture of ES cells. The cells are preferably cultured in a normal medium supplemented with basic fibroblast growth factor (bFGF) and/or stem cell factor (SCF). Usually, the cells are cultured in the presence of fibroblasts as feeder cells derived from mouse embryos, which have been treated with radiation or antibiotics to stop their cell division. Usually, as the fibroblasts as the feeder cells derived from mouse embryos, the STO cell line (ATCC CRL-1503) or the like is commonly used, and, for induction of iPS cells, for example, SNL cells (SNL76/7 STO cells; ECACC 07032801) prepared by stable incorporation of the neomycin resistance gene and the LIF gene into STO cells (McMahon, A. P. & Bradley, A. *Cell* 62, 1073-1085 (1990)) are commonly used. However, in the present invention, since usage of primary fibroblasts derived from mouse embryos (MEFs) shows better improvement of the establishment efficiency of human iPS cells, MEFs are preferably used. Mitomycin C-treated MEFs are commercially available from MILLIPORE and ReproCELL Inc. The co-culture with such feeder cells may be started before, during, or after (e.g., 1 to 10 days after) the contact with the nuclear reprogramming substance(s).

Examples of the method for selecting candidate colonies of iPS cells include methods using drug resistance and reporter activity as indices and methods by visual observation of morphology. Examples of the former method include methods wherein the locus of a gene which is specifically and highly expressed in pluripotent cells (e.g., Fbx15, Nanog or Oct3/4; preferably Nanog or Oct3/4) is targeted by a drug resistance gene and/or a reporter gene to prepare recombinant somatic cells, which cells are used for selection of colonies which are positive for the drug resistance and/or the reporter activity. Examples of such recombinant cells include MEFs derived from mouse wherein the βgeo gene (which encodes a fusion protein of β-galactosidase and neomycin phosphotransferase) was knocked-in into the Fbx15 locus (Takahashi & Yamanaka, *Cell,* 126, 663-676 (2006)) and MEFs derived from a transgenic mouse wherein the green-fluorescent protein (GFP) gene and the puromycin resistance gene were incorporated into the Nanog locus (Okita et al., *Nature,* 448, 313-317 (2007)). On the other hand, examples of the method to select candidate colonies by visual observation of their morphology include the method described in Takahashi et al., *Cell,* 131, 861-872 (2007). Methods using reporter cells are simple and efficient, but, when iPS cells are prepared for the purpose of human therapy, visual selection of the colonies is preferred in view of safety.

The fact that the cells of the selected colonies are iPS cells can be confirmed based on positivity of the Nanog (or Oct3/4) reporter (puromycin resistance, GFP positivity or the like) and visual observation of formation of ES cell-like colonies, and tests such as alkaline phosphatase staining, analysis of ES cell-specific expression of various genes, and transplantation of the selected cells to mice followed by confirmation of formation of teratoma can also be carried out to obtain more accurate results.

III. Method for Inducing Differentiation of Pluripotent Stem Cells to Mast Cells The method for inducing differentiation of pluripotent stem cells to mast cells comprises the following two steps:

(a) culturing human pluripotent stem cells under a condition suitable for promoting differentiation of the human pluripotent stem cells into hematopoietic progenitor cells expressing CD34; and (b) culturing the cells obtained in step (a) in the presence of hematopoietic factors comprising thrombopoietin (TPO) and Flt3 ligand.

Preferably, said hematopoietic factors of step (b) further comprise stem cell factor (SCF) and IL-6. More preferably, the method further comprises the step of proliferating the cells before proceeding to step (b), namely, the method comprises the following three steps:

(a) co-culturing human pluripotent stem cells with cells obtained from the AGM region of a mammalian fetus in the presence of VEGF;

(a') suspension-culturing the cells obtained in step (a) in the presence of the hematopoietic factors comprising TPO, SCF, IL-6 and IL-3 and Flt3 ligand; and (b) suspension-culturing the cells obtained in step (a') in a serum-free medium in the presence of hematopoietic factors comprising TPO, SCF and IL-6, and Flt3 ligand, wherein the hematopoietic factors in the step (b) do not comprise IL-3. In the present invention, VEGF or PDGF may be added in the step of (a').

Here, the term "condition suitable for promoting differentiation of the human pluripotent stem cells into hematopoietic progenitor cells expressing CD34" means e.g. co-culture with cells obtained from the AGM region of a mammalian fetus in the presence of vascular endothelial growth factor (VEGF), or culture on mouse embryonic fibroblasts or OP9 cells, or formation of embryoid bodies and then culture in defined differentiation conditions which may utilize fibronectin, collagen IV or other matrices.

The term "AGM(aorta, gonad and mesonephros) region" means the portion in a fetus surrounded by the dorsal aorta, gonad and mesonephros, which is preferably obtained from a mouse of 10.5 days. The cells separated from the AGM region are preferably treated with γ-ray to remove hematopoietic cells. Specific examples of the cells separated from the AGM region include cells established by the method described in JP 2001-37471 A, which are positive for VECAM-1, CD13 and Sca-1 and produce IL-6 and oncostatin M. Preferably, the cells are AGM-S3 described in JP 2001-37471. During the co-culture, the cells separated from the AGM region preferably exist in excess with respect to the human pluripotent stem cells. Further, the cells separated from the AGM region are preferably subjected to radiation treatment or mitomycin C treatment to eliminate their growth function before the co-culture.

The term "hematopoietic factors" means factors that promote differentiation and growth of blood cells, and examples thereof include stem cell factor (SCF), colony-stimulating factor (CSF), granulocyte colony-stimulating factor (Granulocyte-(G-) CSFs), erythropoietin (EPO), Flt3 ligand, interleukins and thrombopoietin (TPO). Here, interleukins are proteins secreted from leukocytes, and include not less than 30 types of the proteins such as IL-1, IL-2, IL-3, IL-4, IL-5, IL-6, IL-7, IL-8 and IL-9. In the present invention, the term of "cytokines" is not distinguished from "hematopoietic factors". Preferably, the hematopoietic factors are SCF, TPO, Flt3 ligand, IL-3 and IL-6 or SCF, TPO, Flt3 ligand, and IL-6.

The term "serum-free medium" means a medium that does not contain serum derived from an animal. It may contain any one of: albumin or an albumin alternative; transferrin or a transferrin alternative; and insulin or an insulin alternative. In the present invention, a preferred serum-free medium is a medium containing StemSpan® SFEM (Stemcells, Inc.) as an alternative to serum. The medium may also be prepared by adding cytokines to a basal medium, and examples of the basal medium include minimum essential medium (MEM), Dulbecco's modified Eagle's medium (DMEM) and Iscove's modified Dulbecco's medium (IMDM).

In the present invention, if not otherwise specified, the culture medium can be prepared as basal medium. Examples of such basal medium include IMDM medium, medium 199, Eagle's Minimum Essential Medium (EMEM), alpha-MEM medium, Doulbecco's modified Eagle's Medium (DMEM), Ham's F12 medium, RPMI 1640 medium, Fischer's medium, Glasgow MEM, and mixtures thereof. The basal medium may contain serum or cytokines.

The term "suspension culture" means culturing of cells using a non-adherent type culture dish.

In the case of adherent type culture, for the purpose of improving adhesion properties with cells, the surface of the culture dish may be coated with a cell-supporting substance, such as collagen I, collagen IV, gelatin, poly-L-lysine, poly-D-lysine, laminin, fibronectin, or Matrigel™ (Becton, Dickinson and Company).

The Flt3 ligand is a cytokine which can be exemplified by the nucleic acid sequence information shown as NCBI NM_001459, whose receptor is flt3 which is a transmembrane-type tyrosine kinase.

The cytokines used in the present invention, such as VEGF, hematopoietic factors and Flt 3 ligand, may be either a naturally-occurring cytokine or a recombinant cytokine prepared by genetic engineering. It does not need to contain the entire length of the cytokine, and may be a partial protein or peptide containing the region involved in its binding to the receptor. Further, it may be a protein or peptide whose amino acid sequence or spatial structure is modified to an extent at which the binding capacity to the receptor is not impaired. Further, it may be a protein, peptide or agent which can function as an agonist against the receptor of the cytokine.

The concentration of each cytokine is not restricted as long as the cells of interest (mast cells) can be obtained therewith, and may be 5 ng/ml to 50 ng/ml, preferably 10 ng/ml to 20 ng/ml in the case of VEGF; 50 ng/ml to 200 ng/ml, preferably 100 ng/ml in the case of SCF; 5 ng/ml to 50 ng/ml, preferably 10 ng/ml in the case of IL-3; 50 ng/ml to 200 ng/ml, preferably 100 ng/ml in the case of IL-6; 5 ng/ml to 50 ng/ml, preferably 10 ng/ml in the case of the Flt3 ligand; and 5 ng/ml to 50 ng/ml, preferably 10 ng/ml in the case of TPO.

The mast cells express at least the IgE receptor, c-kit and tryptase; preferably express chymase at the same time; more preferably express Cathepsin-G, CD203c, Carboxypeptidase-A and CD88.

In terms of the length of the period of each step, the step "(a) co-culturing human pluripotent stem cells with cells separated from the AGM region of a mammalian fetus in the presence of VEGF" is carried out for not less than 10 days, preferably 10 to 18 days. The step "(a') proliferating the cells by suspension culture in the presence of VEGF and hematopoietic factors" is carried out for not less than 5 days, preferably 5 to 7 days. The step "(b) culturing the obtained cells in a serum-free medium in the presence of hematopoietic factors and the Flt3 ligand" is carried out for not less than 28 days, preferably 28 to 140 days.

IV. Screening Method

Method for Screening a Pharmaceutically Effective Substance

The present invention provides a method for screening a substance which suppresses activation of human mast cells, by contacting the mast cells obtained as described above with test substances, and selecting a substance having at least one of the actions against mast cells selected from the group consisting of (a) apoptosis induction, (b) degranulation inhibition and (c) inhibition of production of inflammatory mediators.

The test substance may be any known or novel compound, and examples thereof include nucleic acids; carbohydrates; lipids; proteins; peptides; organic low molecular weight compounds; compound libraries prepared using the combinatorial chemistry technology; random peptide libraries prepared by solid phase synthesis or the phage display method; and natural components derived from microorganisms, animals, plants, marine organisms and the like.

In the screening method, the mast cells are contacted with a test substance and the degree of (a) apoptosis induction, (b) degranulation inhibition or (c) inhibition of production of inflammatory mediators is measured. Then, the degree is compared to the degree in the case of mast cells without contacting the test substance, and a test substance which significantly changes the degree of (a) apoptosis induction, (b) degranulation inhibition and/or (c) inhibition of production of inflammatory mediators as compared to the case without contacting the test substance is selected as an effective component.

Here, examples of the method for detection of apoptosis include methods using nucleic acid staining reagents such as propidium iodide (PI) and Hoechst 33258; and methods for detection of changes in the membrane structure using fluorescently-labeled annexin V and the like. Among these, methods using propidium iodide (PI) and FITC-labeled annexin V are preferred.

Examples of the method for detection of degranulation include the method where IgE antibody is allowed to bind to the mast cells, and the resultant is stimulated by being brought into contact with an antigen, followed by detection of inflammatory mediators released by the stimulation. Examples of the inflammatory mediators include, but are not limited to, proteins in cell granules such as histamine, beta-hexosaminidase and tryptase; and physiologically active substances that are biosynthesized in response to stimulation, such as IL-6, TNFα and leukotriene B4. Alternatively, the mast cells can be also stimulated by a pathway in which IgE antibody is not involved. That is, various physiological stimulations other than antigens can also cause mast cells to release inflammatory mediators. Examples of such substances that stimulate mast cells to cause their reaction include antigenic substances such as DNP-HAS (dinitrophenol-human serum albumin); anti-IgE antibody; anti-IgE receptor antibody; complement components such as C3a and C5a; neuropeptides such as substance P and CGRP; ionomycin; and ATP. The degranulation can also be detected by, as an alternative to measurement of inflammatory mediators, surface plasmon resonance (SPR) which detects the large change in the resonance angle produced by mast cells upon antigenic stimulation after sensitization with IgE antibody or upon stimulation with non-IgE stimulus.

Suppression of production of inflammatory mediators can be detected based on the amount of the inflammatory mediators existing in the mast cells.

The thus screened test substances can be used as therapeutic agents for bronchial asthma, allergic disease and atopic dermatitis.

Method for Screening a Tailor-Made Drug

In the present invention, the term "tailor-made drug" means a therapeutic agent most suitable for each individual patient having unique characteristics.

The mast cells obtained by differentiation of iPS cells produced from somatic cells of a subject suffering from bronchial asthma, allergic disease or atopic dermatitis are brought into contact with known therapeutic agents, and a therapeutic agent having at least one of the actions against mast cells selected from the group consisting of (a) apoptosis induction, (b) degranulation inhibition and (c) inhibition of production of inflammatory mediators is selected. Thus, the screened therapeutic agent can be an optimal therapeutic agent for the subject from whom the iPS cells have been established.

Examples of the known therapeutic agents include, but are not limited to, chemical mediator release inhibitors (e.g., sodium cromoglycate (Intal), tranilast (Rizaben), amlexanox (Solfa) and pemirolast potassium (Alegysal)); chemical mediator receptor antagonists (e.g., (1) antihistaminic agents such as d-chlorpheniramine maleate (Polaramine), clemastine fumarate (Tavegyl), ketotifen fumarate (Zaditen), azelastine hydrochloride (Azeptin), oxatomide (Celtect), mequitazine (Zesulan, Nipolazine), emedastine fumarate (Daren, Remicut), cetirizine hydrochloride (Zyrtec), Levocabastine hydrochloride (Livostin), fexofenadine hydrochloride (Allegra), olopatadine hydrochloride (Allelock), (2) thromboxane A2 antagonists such as Ramatroban (Baynas), (3) leukotriene antagonists such as pranlukast hydrate (Onon)); Th2 cytokine inhibitors (e.g., suplatast tosylate (IPD)); steroid drugs (e.g., (1) topical steroid agents such as beclometasone dipropionate (Beconase, Aldecin, Rhinocort), flunisolide (Synaclyn) and fluticasone propionate (Flunase), (2) oral steroid drugs such as Celestamine (chlorpheniramine maleate-containing drug); autonomic drugs (e.g., (1) α stimulators such asnaphazoline nitrate (Privina), tetrahydrozoline nitrate (Narbel), oxymetazoline hydrochloride (Nasivin), tramazoline hydrochloride (Towk), (2) anticholinergic drugs such as ipratropium bromide (Atrovent) and flutropium bromide (Flubron)); and biologics (e.g., Neurotropin, Asthremedin and MS antigen)).

The mutation of the isoleucine which is the 181st amino acid of the FcεRI beta chain to leucine is suggested to be strongly correlated with atopic disposition. Thus, gene mutation may be related to atopic disposition. Therefore, the present invention provides a method for screening of a therapeutic agent having an action specifically against a genetic disease, wherein iPS cells obtained from a patient having a mutation(s) in at least the FcεRI beta chain are allowed to differentiate into mast cells, followed by screening of the therapeutic agent using the resulting mast cells.

The present invention will now be described in more detail by referring to Examples, but, needless to say, the present invention is not restricted to these.

EXAMPLES

Example 1

Cells

AGM-S3 cells established and cultured by the conventional method described below (JP 2001-37471 A). Briefly, the AGM-S3 cells were established by a process where the AGM region was excised from a mouse fetus and subjected to γ-ray irradiation to remove hematopoietic cells, followed by cloning by the limiting dilution method. These AGM-S3 cells are known to have an activity to support the growth of human haematopoietic stem cells. A photograph showing the AGM-S3 cells is shown in FIG. 1A. On the other hand, iPS cells (253G1) were provided from Dr. Yamanaka and cultured by the conventional method described below (Nakagawa M, et al., *Nat Biotechnol* 26 (1), 101, 2008). Briefly, the 253G1 cells were established by introducing Oct3/4, Sox2 and Klf4 to fibroblasts derived from human dermis. The 253G1 cells can also be obtained from RIKEN CELL BANK. A photograph showing the 253G1 cells is shown in FIG. 1B.

Immunofluorescence Staining

Mast cells derived from iPS cells were picked and centrifuged onto glass slides. The obtained Cytospin preparations were then stained with May-Grünwald-Giemsa, acidic toluidine blue, and alcine blue. For mast cell specific tryptase and chymase assays, an immunofluorescence staining method was used, as previously reported (Ma F, et al., *Proc Natl Acad Sci US* 105, 13087, 2008). Briefly, mouse- and goat-anti-human tryptase monoclonal antibodies (mAbs) (DakoCytomation and Santa Cruz, respectively), mouse-anti-human chymase mAb (Chemicon, Temecula, Calif.), and mouse- or rabbit-anti-human c-Kit (Nichirei and IBL, respectively) were used.

Method of Induction of Differentiation of iPS Cells into Mast Cells

Step 1

Figure 2:
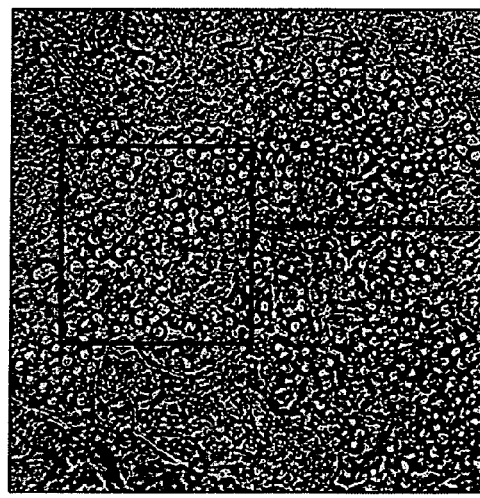
FIG. 2 shows phase contrast micrographs of 253G1 cells after co-culture with AGM-S3 cells using DMEM supplemented with 20 ng/ml human VEGF and 15% fetal bovine serum (FBS) for 14 days. The right panel shows a magnified image of the area surrounded by the frame in the left panel.
Figure 2:
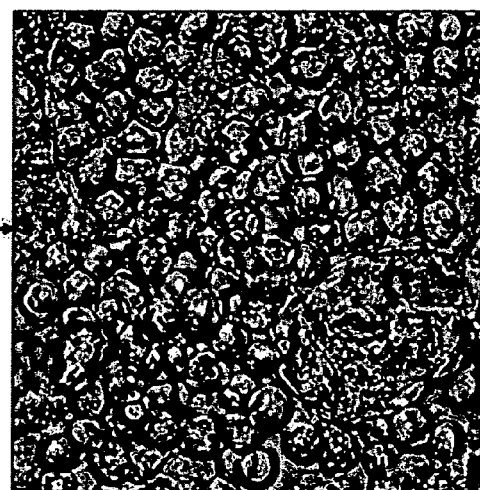

On AGM-S3 cells that had been preliminarily cultured and subjected to radiation treatment, 20 to 30 colonies of 253G1 cells were placed, and the cells were cultured using, as a medium, DMEM supplemented with 20 ng/ml human VEGF (WAKO) and 15% FBS for 14 days, thereby hematopoietic progenitor cells were developed. During the culture, the medium was replaced every 3 days. Photographs of the established cells are shown in FIG. 2. Here, similar cells were obtained also by using, as a medium, IMEM (Improved Minimal Essential Medium) supplemented with 10 ng/ml human VEGF and 10% FBS. Therefore, it was found that either medium can be used.

Step 2

The cells established in Step 1 were dispersed in the plate, and grown for 5 to 7 days by suspension culture in a medium, IMDM supplemented with, 100 ng/ml human SCF (WAKO), 10 ng/ml human IL-3, 100 ng/ml human IL-6, 10 ng/ml human Flt3-ligand (FL) (R&D Systems), 10 ng/ml human thrombopoietin (TPO) and 10% FBS and with or without 10 ng/ml human VEGF.

Step 3

Figure 3:
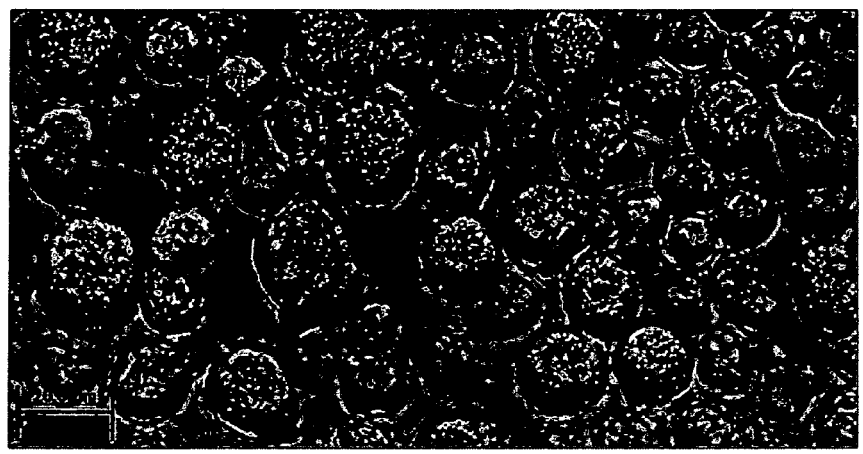
FIG. 3 shows a phase contrast micrograph of mast cells which were established by culture using a serum-free medium supplemented with 100 ng/ml SCF, 100 ng/ml human IL-6 and 10 ng/ml human Flt3-ligand for 52 days.

The medium was replaced with serum-free IMDM supplemented with 100 ng/ml SCF, 100 ng/ml human IL-6, 10 ng/ml human FL and 10% StemSpan® SFEM, and the cells were cultured for over 4 weeks, thereby mast cells were established. During the culture, the medium was replaced twice a week. A photograph of the established cells at 52 days after the initiation of Step 1 is shown in FIG. 3. The yield of the mast cells was over 95%. Here, by using a medium further containing 10 ng/ml human IL-3 and 10 ng/ml human TPO, mast cells of the same quality were obtained at a high yield.

Evaluation of the Mast Cells

Figure 4:
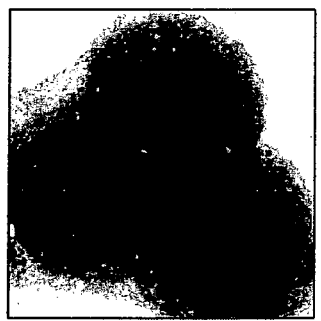
FIG. 4 shows micrographs of established mast cells stained with May-Giemsa (A), Toluidine Blue (B) and Alcian Blue (C) solutions.
Figure 4:
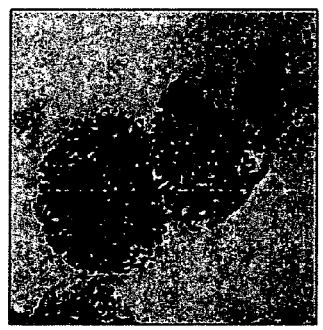
Figure 4:
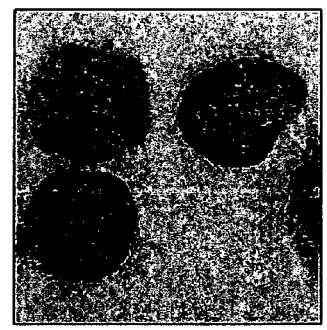
Figure 5:
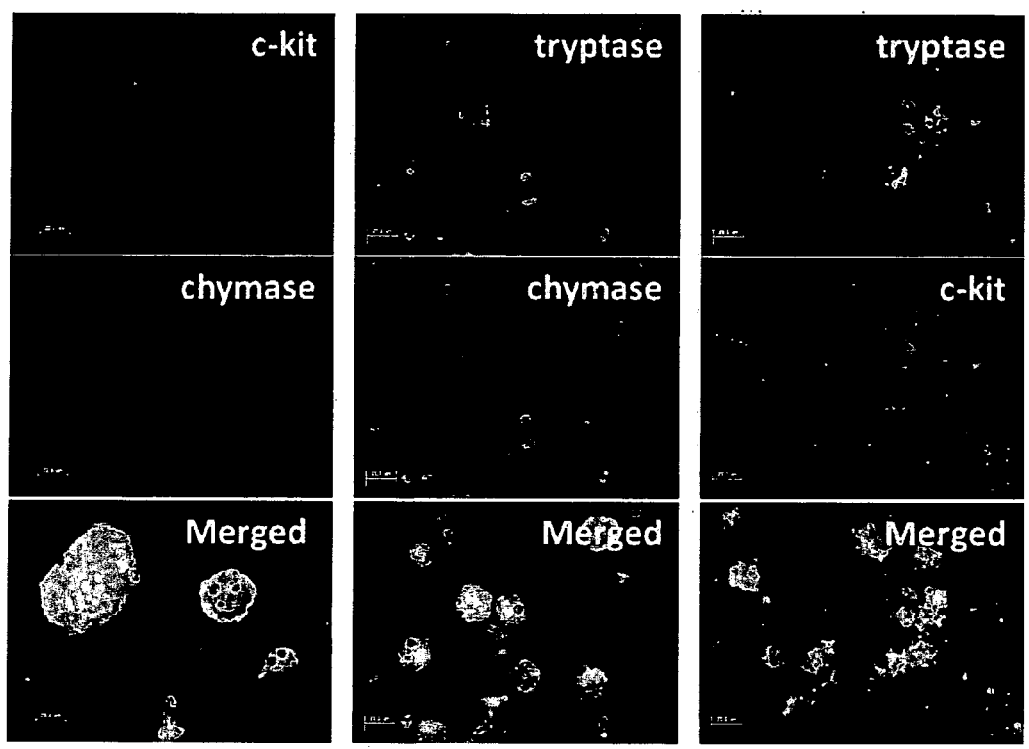
FIG. 5 shows micrographs obtained by immunostaining of established mast cells with anti-c-kit antibody, anti-chymase antibody and anti-tryptase antibody, and merged images of these images.
Figure 6:
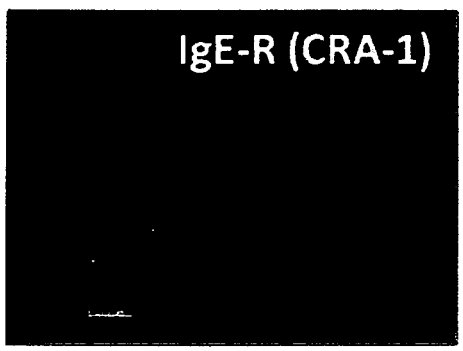
FIG. 6 shows micrographs obtained by immunostaining of established mast cells with anti-IgE receptor antibody (CRA-1), anti-Cathepsin-G antibody, anti-CD203c antibody, anti-Carboxypeptidase-A antibody and anti-CD88 antibody.
Figure 6:
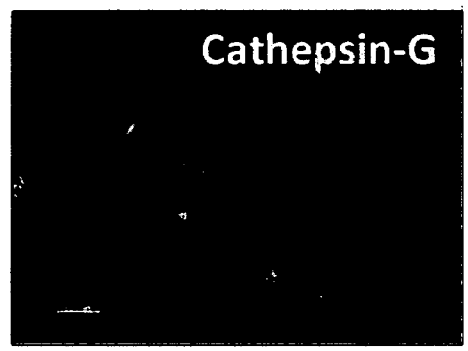
Figure 6:
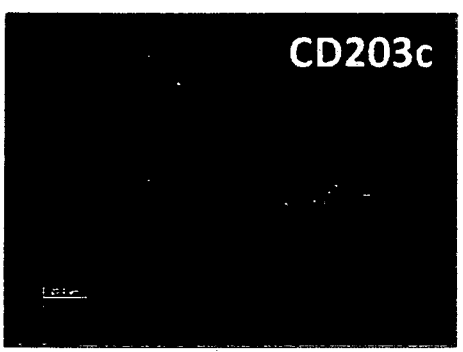
Figure 6:
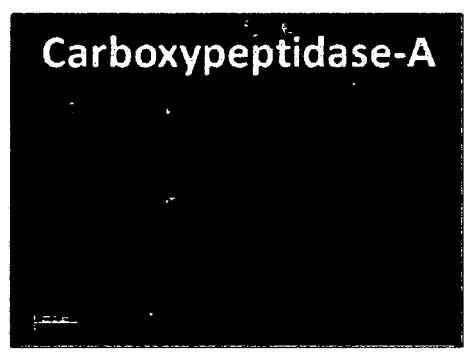
Figure 6:
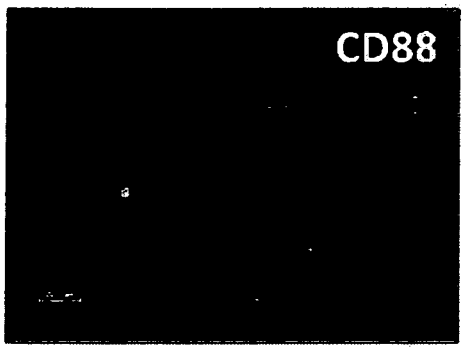

The thus established mast cells were stained with a May-Giemsa, Toluidine Blue or Alcian Blue solution. Stained images are shown in panels A, B and C in FIG. 4, respectively. Further, immunostaining was carried out using antibodies against c-kit, tryptase and chymase. Stained images obtained by the immunostaining, and co-stained images by combinations of the antibodies are shown in FIG. 5. Further, immunostaining was carried out using antibodies against IgE-R (CRA-1), Cathepsin-G, CD203c, Carboxypeptidase-A and CD88. Stained images are shown in panels A, B, C, D and E in FIG. 6, respectively. The cells were positive for all the marker genes.

Example 2

Cells

Human embryonic stem cells (ESCs) of H1, at passage 32 to 36, were cultured on mouse embryonic fibroblasts (MEF) in KO medium consisting of DMEM/F12, 20% KO-SR (Invitrogen), 1 mM glutamine, 0.1 mM β-mercaptoethanol, 1% nonessential amino acids (Invitrogen) and 4-5 ng/ml basic-fibroblast growth factor (b-FGF) (WAKO, Osaka), as previously described (J A Thomson, et al., Science 282, 1145, 1998 or F Ma, et al., Proc Natl Acad Sci US 105, 13087, 2008). The H1 line was passaged by mechanical dissociation weekly. The other hESC (human embryonic stem cell) lines, KhES-1 and KhES-3, were provided by Dr. N. Nakatsuji (H Suemori, et al., Biochem Biophys Res Commun. 345, 926, 2006). They were at passage 18 to 20 and 20 to 22, respectively, and maintained and passaged weekly as described. The use of hESCs was approved by the committee of the Minister of Education, Culture, Sports, Science, and Technology of Japan. AGM-S3 cells were described above.

Morphological Observations and Immunofluorescence Staining

On given days, cells in MC-cultures were picked and centrifuged onto glass slides. The obtained Cytospin preparations were then stained with May-Grünwald-Giemsa, acidic toluidine blue, and alcine blue. For MC specific tryptase and chymase assays, an immunofluorescence staining method was used, as previously reported (Ma F, et al., Proc Natl Acad Sci US 105, 13087, 2008). Mouse- and goat-anti-human tryptase monoclonal antibodies (mAbs) (DakoCytomation and Santa Cruz, respectively), mouse-anti-human chymase mAb (Chemicon, Temecula, Calif.), and mouse- or rabbit-anti-human c-Kit (Nichirei and IBL, respectively) were used for these assays. MCs were also observed by transmission electron microscope.

Flow Cytometry

Cells were preincubated with normal rabbit serum to block non-specific binding and then stained with various antibodies conjugated with fluorescein isothiocyanate (FITC), phycoerythrin (PE) or allophycocyanin (APC). Stained cells were washed with phosphate buffered saline (PBS) and analyzed using a FACScalibur cytometry system (BD Biosciences, San Jose, Calif.). Propidium iodide (PI)-stained dead cells were gated out. Data were analyzed with a Flowjo software. mAbs against CD45 (DakoCytomation), c-Kit (Nichirei), CD31 (BD Biosciences), FcεRI (CRA-1, eBioscience), CD203c (Beckman Coulter), CD88 (Serotec) and HLA-DR (BD Biosciences) were used in this analysis.

Activation of MCs

For stimulation, substance P (Sigma), compound 48/80 or control medium was added to a 25 µl cell suspension ($4 \times 10^5$ MCs/ml) in 96-well plates, and incubated for further 15 min at 37° C. The reaction was stopped by adding 200 µl ice-cold buffer. The cells were separated by centrifugation at 300×g for 7 min at 4° C., and the supernatant was collected. The cell pellet was resuspended in 200 buffer containing 0.5% Triton-X and 0.1% bovine serum albumin (BSA), quick frozen in liquid nitrogen and thawed 4 times. After centrifugation at 12,000×g for 15 min at 4° C., the soluble extract was collected. Histamine levels were measured by an ELISA histamine kit (Beckman Coulter)

Method of Induction of Differentiation of iPS Cells into Mast Cells

Figure 7:
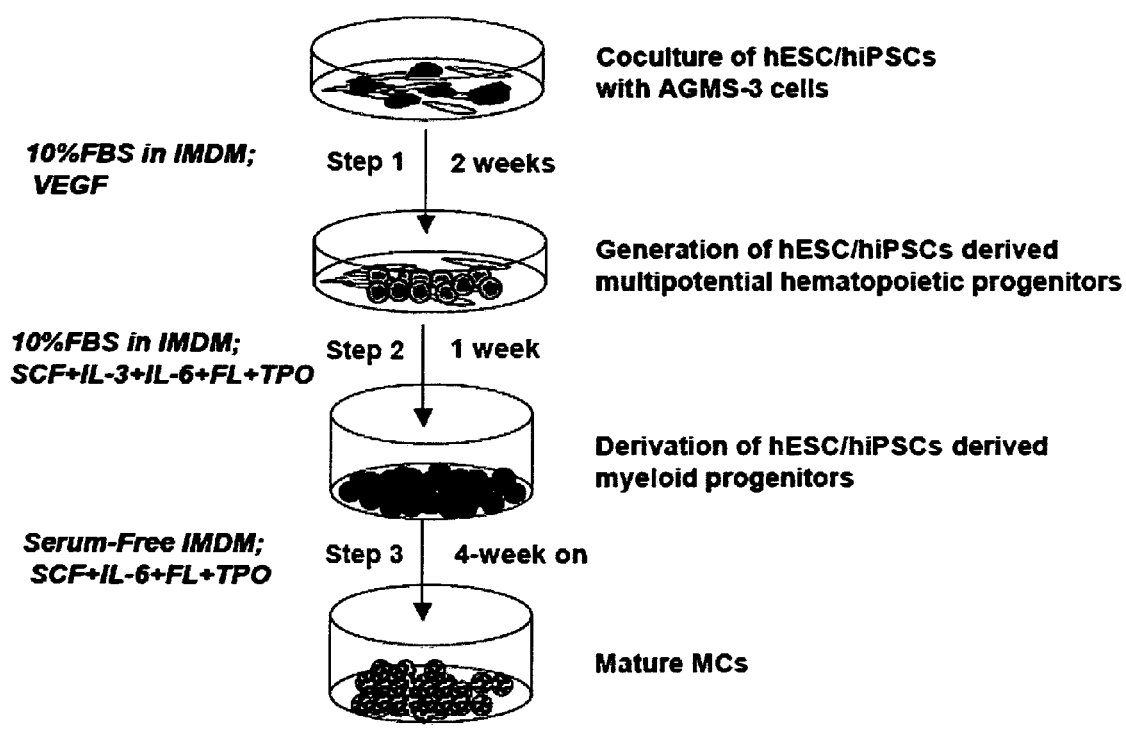
FIG. 7 shows a programmatic illustration of the induction of mature mast cells (MCs) from human pluripotent stem cells.

The scheme of three-step culture method for producing mature mast cells (MCs) is shown in FIG. 7.

Step 1

Figure 8:
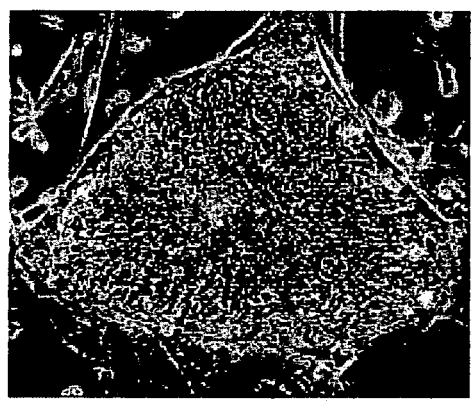
FIG. 8 shows phase contrast micrographs of (A) undifferentiated hESC (H1) colony at day 3 of co-culture, (B) a robust growth of cobblestone like cells at day 14 of co-culture, and (C) enlarged photo of the same culture as in (B), showing cobblestone like cells.
Figure 8:
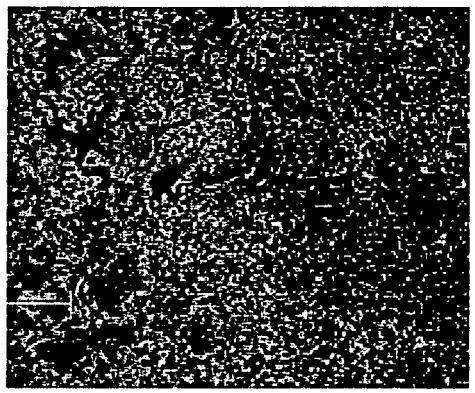
Figure 8:
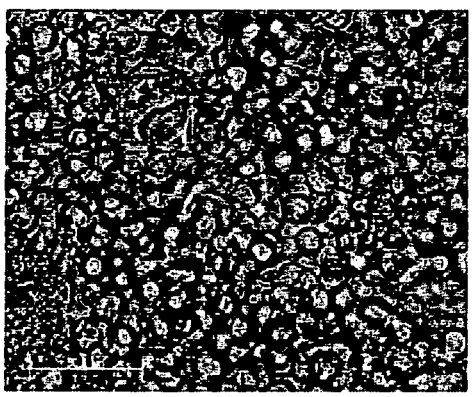

Initially, $1 \times 10^5$ irradiated AGMS-3 cells were plated in a 6-well, suitable for allowing 1.5 to $1.6 \times 10^4$ undifferentiated hESCs (approximately 30 colonies, 500 to 2000 cells per colony) to grow. To ensure a fluent adaptation, a medium for maintaining hESC was added during the first 3 days in the co-culture. When undifferentiated hESC colonies began to enlarge (FIG. 8A), the culture medium was changed to Iscove's Modified Dulbecco's Medium (IMDM) containing 10% fetal bovine serum (FBS), supplemented with a cocktail of 5.5 µg/mL human transferrin (Sigma), 2 mM L-glutamine, 50 µg/mL ascorbic acid and 20 ng/ml vascular endothelial growth factor (VEGF) (WAKO, Osaka). The culture medium was replaced every 2 days. During continuous culture, hESC colonies began to differentiate towards a mesoderm type aggregation with the outskirt looked like to be endothelial ones. At days 8 to 10 of co-culture, gathering and expansion of some cobble stone-like cells could be observed around these outskirt areas (FIGS. 8B and 8C), most of them being $CD34^+$ progenitors with a hemagiaoblastic cell property. At days 13 to 15, the co-cultures were treated with 0.25% trypsin/EDTA solution (Wako) and whole cells, including hematopoietic progenitor cells, were collected for further use in Step 2. $1.48 \pm 0.48 \times 10^6$ total cells (H1 line, n=9; with $14.0 \pm 3.1\%$ $CD34^+$ cells, n=3) were generated from one single 6-well at day 14 of co-culture. These day 14 co-cultured cells produced $121.3 \pm 5.1$ hematopoietic colonies/$2.5 \times 10^4$ cells in clonal culture. However, because of the culture condition lessened after 2 weeks, these hematopoietic cells could not further proliferate and undergo maturation in the co-culture.

Step 2

Figure 9:
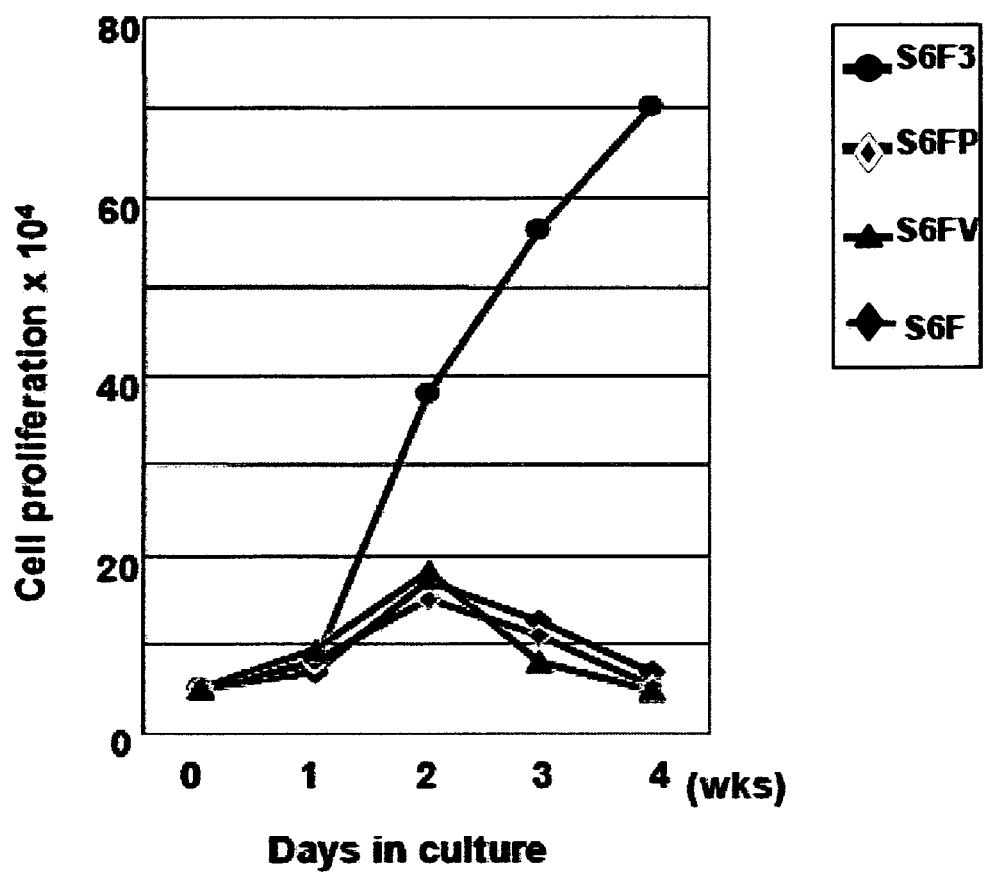
FIG. 9 shows graph of cell proliferation in step 2 with or without IL-3. $5 \times 10^5$ cells in the co-culture of hESCs (H1) and AGMS-3 cells (step 1) were replaced in suspension culture consisting IMDM, 10% FBS (F) and various cytokine combinations (step 2). S, 6, 3, V, and P means SCF, IL-6, IL-3, VEGF, and platelet derived growth factor (PDGF), respectively.

To generate mature MCs from hESC-derived hematopoietic progenitor cells, in this step, total co-cultured cells obtained from Step 1 were cultured in non-adhesion 35 mm dishes (Sumilon, surfaces of the plates are resistant to cell adhesion) nurtured by IMDM with 10% FBS and a cocktail of cytokines favoring hematopoietic progenitor cell development (SCF, IL-3, IL-6, FL, TPO). After 7 days of the culture, most of the cells proliferated were hematopoietic cells with a property of myeloid progenitors. The cells expanded to $1.75 \pm 0.6 \times 10^6$ (n=5) from total co-cultured cells in one 6-well at day 7, which was 29 to 117-fold from initial number of undifferentiated hESCs. The concentration of $CD34^+$ cells was 9.1-fold. In this step, combinations with IL-3 greatly supported cell proliferation, while other combinations (PDFG or VEGF) without IL-3 yielded little cell proliferation (FIG. 9), indicating a critical role for IL-3 in embryonic hemastopoiesis. However, after one week in this IL-3-oriented culture, most of the cells shared a phenotype of myeloid progenitors and continuously differentiated to granulocytes and macrophages, but few c-kit+ mast cells. For this reason, IL-3 was excluded in Step 3.

Step 3

The hESC-derived progenitor cells were shifted to a serum-free MC culture, in IMDM and 10% of SFEM (Stem Cells Tech.) with the addition of SCF, FL, IL-6 and TPO. Half of the volume of culture medium was replaced with fresh medium twice a week. In this step, total cell proliferation gradually decreased while the proportion of c-kit+/tryptase+/chymase+ MCs increased. The purity of these mature MCs reached approximately 80% at 8 to 10 weeks (FIGS. 10A and 10G to 10L) and almost 100% at 15 to 20 weeks.

Evaluation of the Mast Cells

Figure 10:
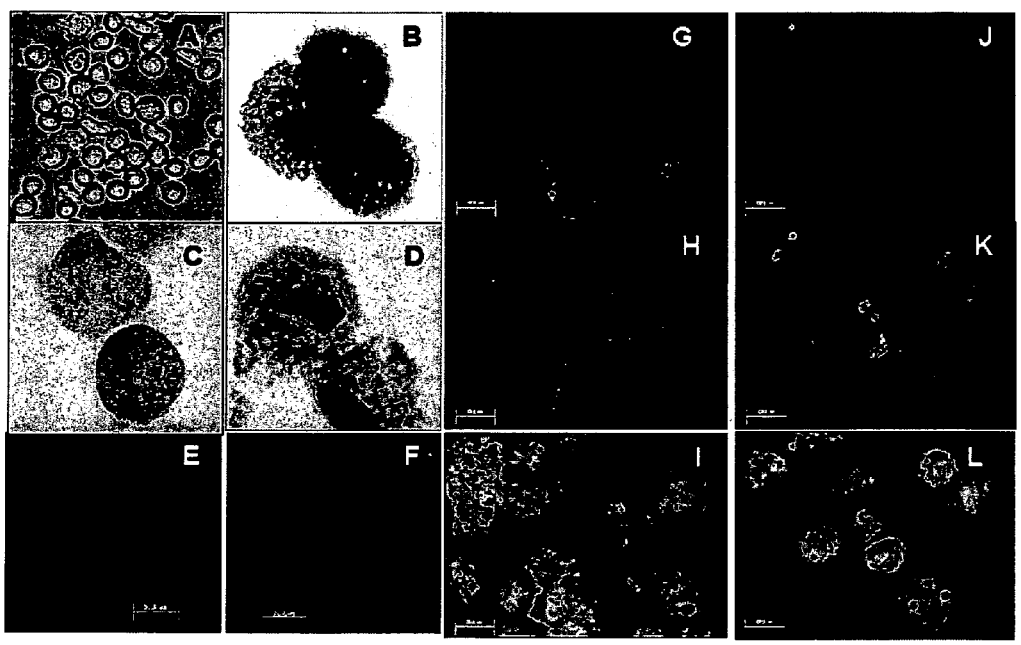
FIG. 10 shows (A) phase contrast micrographs of MCs derived from hESCs (H1) at 10-week in MC-culture, and micrographs obtained by immunostaining of the mast cells with (B) May-Grunwald-Geimsa, (C) toluidine blue, (D) alcian blue, (E) human carboxypeptidase-A, (F) human cathepsin-G, (G) c-Kit, (H) tryptase, (J) c-Kit, and (K) chymase, and (I) a merged image of (G) and (H), and (L) a merged image of (G) and (H).
Figure 11:
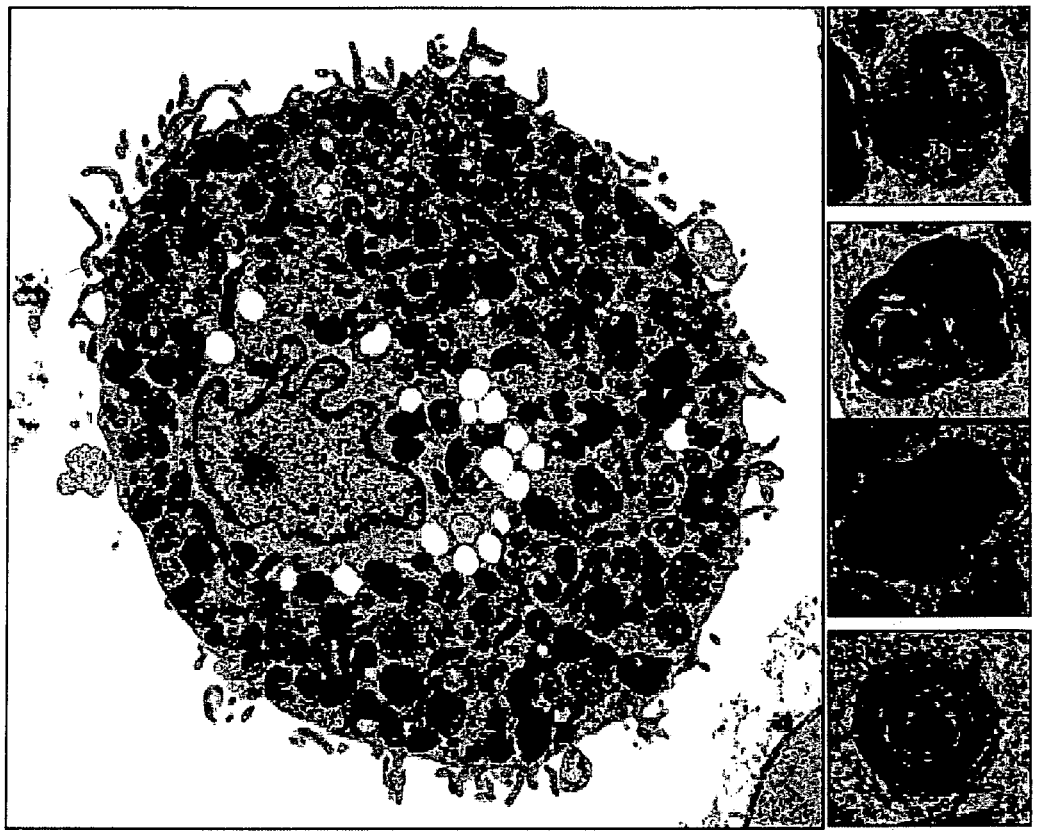
FIG. 11 shows photos of 10-week hESC-MC by transmission electron microscope.
Figure 12:
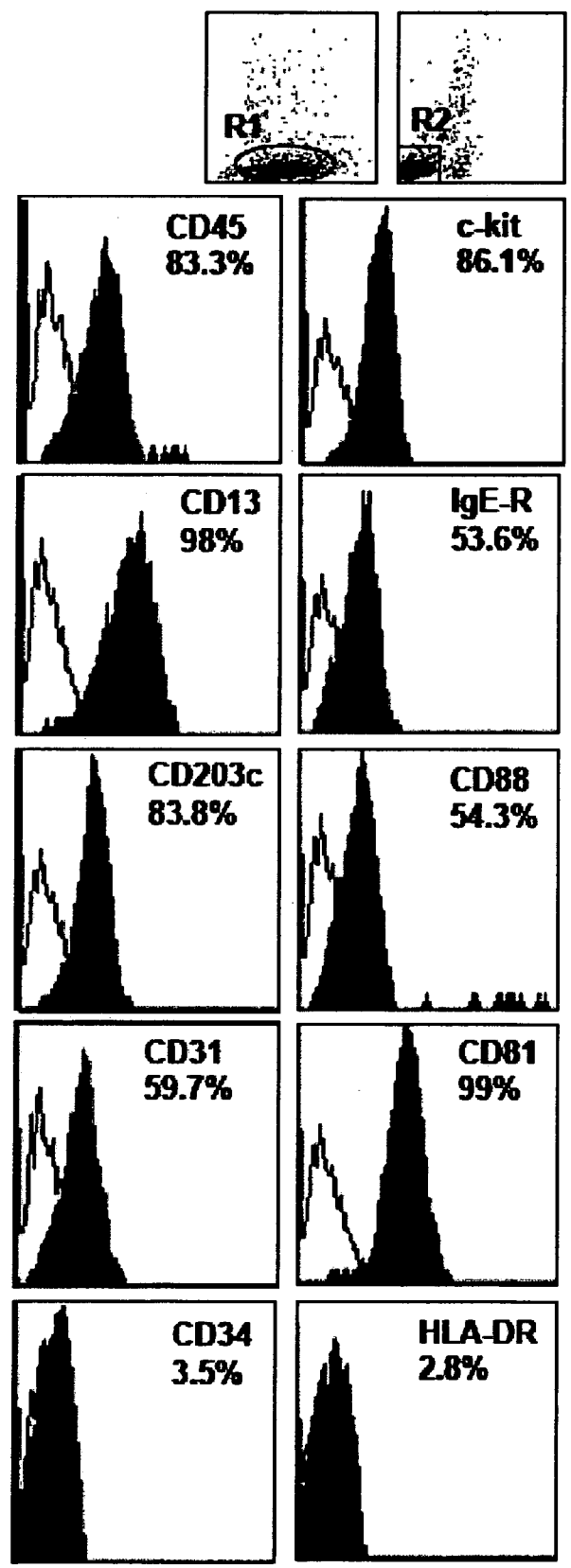
FIG. 12 shows flow cytometric profiles of hESC (H1)-MCs.
Figure 13:
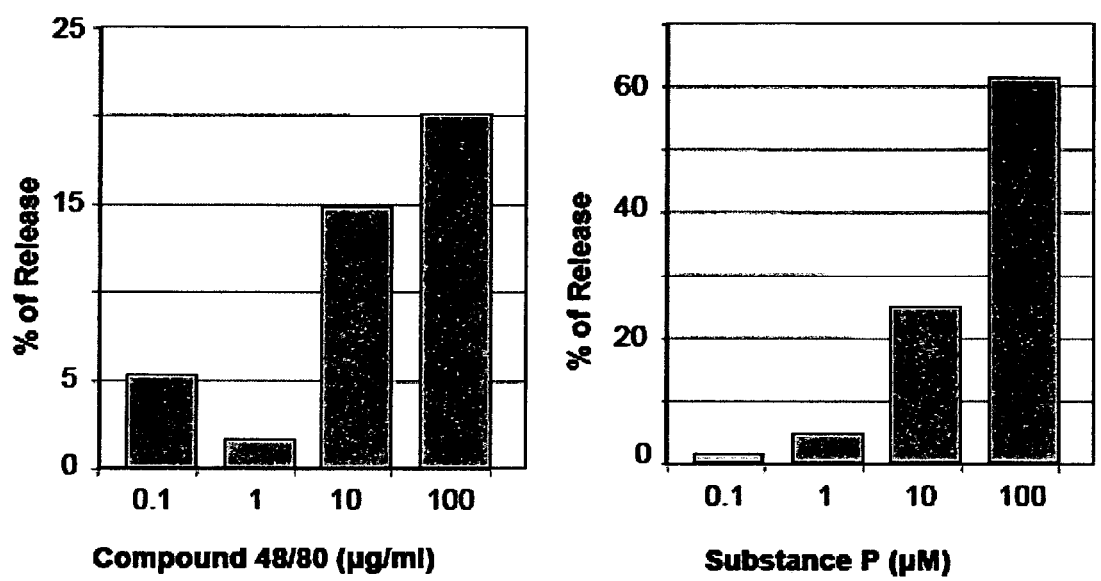
FIG. 13 shows graphs of histamine release from hESC-MCs upon stimulation of compound 48/80 and substance P.
Figure 14:
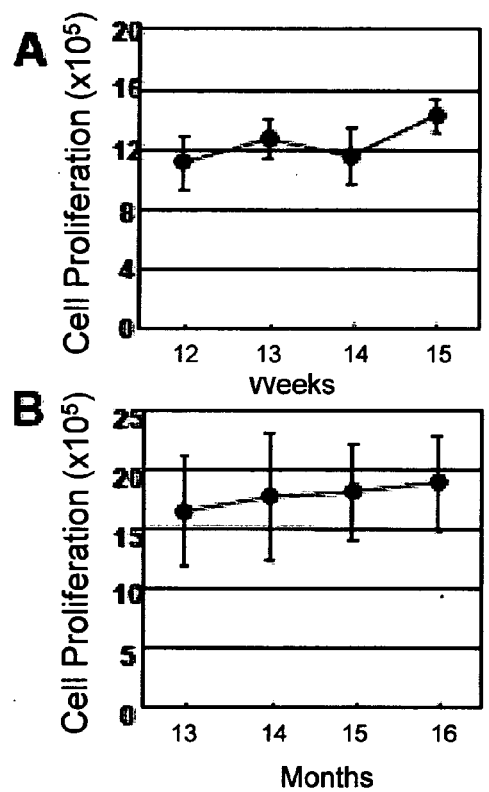
FIG. 14 shows (A) and (B) graph of growth of hESC-MCs in long-term culture, and (C) and (D) flow cytometric profiles about c-Kit and FcεRI of hESC-MCs at 15 months of MC-culture.
Figure 14:
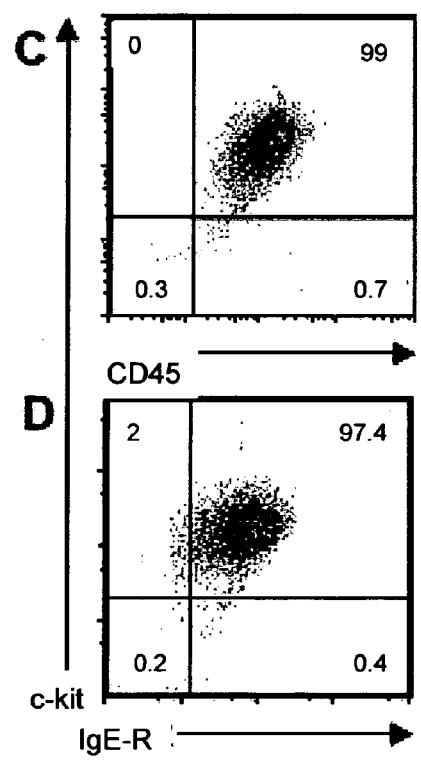

Morphologically, mature hESC-MCs typically revealed huge in size (average 18.7±5.8 μm in diameter, n=12), held rough dense granules and 1-3 lobed nuclear, and shared a basophilic staining property by May-Grunwald-Geimsa staining (FIG. 10B). They also revealed metachromatic staining pattern to toluidine blue and alcian blue stainings (FIGS. 10C and 10D, respectively) and were positively stained with antibodies to human carboxypeptidase-A and cathepsin-G (FIGS. 10E and 10F, respectively). Transmission electron microscope observation showed that the hESC-MCs held abundant granules with various densities and well-developed mitochondria. The scrolling shaped granules, which are typical for human MCs, could be found (FIG. 11). Flow cytometric analysis revealed that these hESC-MCs highly expressed c-Kit, CD45, CD13, CD81, moderately CD31 and a high affinity IgE receptor (FcεRI), but not CD34 and HLA-DR, identical to human mature MCs (FIG. 12). Interestingly, these hESC-derived MCs also coexpressed CD88 and CD203c, both of which have been recognized as the specific markers for human skin-derived connective-tissue type mast cells (CT-MCs). These results indicated that hESC-MCs developed in this Example retained the phenotype of human CT-MCs. Furthermore, hESC-MCs displayed dose-dependent degranulation in response to substance P and compound 48/80 to release histamine (FIG. 13). Besides, hESC-MCs presented longevity in this culture, so far being over 19 months at a low but continuous proliferation rate with no loss of MC properties (FIG. 14). These results provided evidence that MCs produced from hESCs in the present culture system functionally mature CT-MCs, not only upon the fact that they expressed characteristic proteases but also because of their ability to degranulate upon specific pharmacological stimulations.

Example 3

Cells

Human iPSC lines, 253G1 (transfected by 3 factors, Oct4, Sox2 and Klf4) (Nakagawa M, et al., *Nat Biotechnol* 26 (1), 101, 2008) and 201B6 (transfected by 4 factors, Oct4, Sox2, Klf4 and c-Myc) (Takahashi K, et al., *Cell* 131, 861, 2007) were provided by Dr. Yamanaka S. These hiPSC lines were maintained and passaged as reported.

Comparison of Mast Cells Derived from Various Pluripotent Stem Cells

Figure 15:
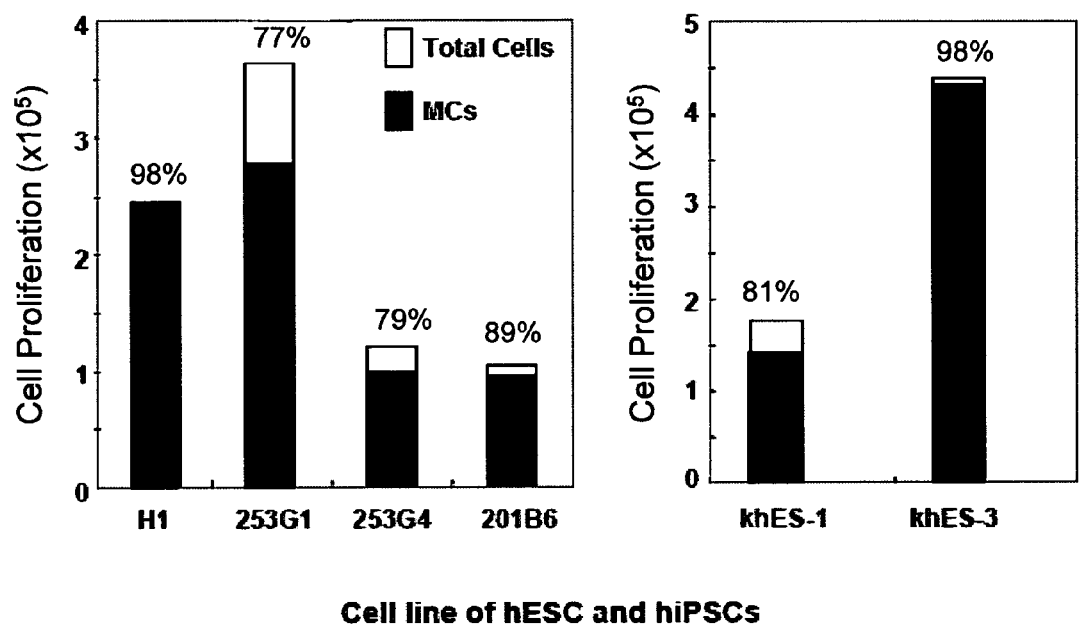
FIG. 15 shows graphs of potentials of various hESCs and hiPSCs (human iPS cells) to produce MCs. Blank and black bars show total cells and c-Kit positive MCs, respectively, at 10-week in MC-culture of hESCs (H1, KhES-1 and KhES-3) and hiPSCs (253G1, 253G4 and 201B6).

Mature MCs were made from various hESC lines (KhES-1 and KhES-3) and hiPSC lines (253G1, 253G4 and 201B6) in the same way as described above. MCs derived from all hESC and hiPSC lines showed the same phenotype to H1 cell line-derived MCs in morphological observations, metachromatic staining pattern to toluidine blue and alcian blue stainings, expression of c-Kit, tryptase, chymase, FcεRI, carboxypeptidase-A, cathepsin-G CD88 and CD203c and flow cytometric profiles, although there was quantitative deviations among cell lines (FIG. 15).

Thus, the culture system of the present invention using the three-step culture method efficiently produced a number of functionally mature MCs with a purity of almost 100% from both hESCs and iPSCs, which should provide a novel method to help developing drugs to cure MC-related disorders, especially various allergic diseases. More importantly, generation of patient-tailored hiPSC-MCs will be an ideal model to uncover the mechanisms controlling those abnormalities with genetic relation to MC development and finally provide the most suitable therapies to the individual patients.

INDUSTRIAL APPLICABILITY

According to the present invention, human mast cells can be efficiently produced from human pluripotent stem cells. Therefore, the present invention is very useful for screening of therapeutic agents for allergic diseases using human mast cells and for selection of therapeutic agents for the so-called tailor-made medicine in which, by using human mast cells established from an individual patient, a therapeutic agent most suitable for the individual is selected.

The invention claimed is:

1. A method for producing human mast cells from human pluripotent stem cells with not less than 77% efficiency, comprising the steps of:
   (a) culturing human pluripotent stem cells under a condition suitable for promoting differentiation of the human pluripotent stem cells into hematopoietic progenitor cells expressing CD34;
   (b) suspension-culturing the cells obtained in step (a) in the presence of hematopoietic factors comprising TPO, Flt3 ligand, SCF, IL-6 and IL-3 for 5 to 7 days; and
   (c) suspension-culturing the cells obtained in step (b) in a serum-free medium containing hematopoietic factors comprising TPO, Flt3 ligand, SCF and IL-6 but not comprising IL-3,
   wherein human mast cells are produced with not less than 77% efficiency.

2. The method according to claim 1, wherein step (a) comprises co-culture with cells obtained from an AGM region of a mammalian fetus in the presence of vascular endothelial growth factor (VEGF).

3. The method according to claim 2, wherein said cells obtained from the AGM region of a mammalian fetus are AGM-S3 cells.

4. The method according to claim 1, wherein said human pluripotent stem cells are human induced pluripotent stem cells.

5. The method according to claim 1, wherein the produced human mast cells express c-kit, tryptase, chymase, IgE receptor, Cathepsin-G, CD203c, Carboxypeptidase-A and CD88.

* * * * *